(12) United States Patent
Dahm

(10) Patent No.: US 6,582,904 B2
(45) Date of Patent: *Jun. 24, 2003

(54) METHOD OF QUANTIFYING TUMOUR CELLS IN A BODY FLUID AND A SUITABLE TEST KIT

(76) Inventor: Michael W. Dahm, Gleimstr. 2, D-81677 Munich (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 100 days.

(21) Appl. No.: 09/068,821
(22) PCT Filed: Nov. 14, 1996
(86) PCT No.: PCT/DE96/02183

§ 371 (c)(1),
(2), (4) Date: May 14, 1998

(87) PCT Pub. No.: WO97/18322

PCT Pub. Date: May 22, 1997

(65) Prior Publication Data

US 2002/0012969 A1 Jan. 31, 2002

(30) Foreign Application Priority Data

Nov. 16, 1995 (DE) .......................................... 195 42 795

(51) Int. Cl.[7] ............................ C12Q 1/68; C12P 19/34; C07H 21/04; C07H 21/02; C12N 9/12
(52) U.S. Cl. ........................ 435/6; 435/91.2; 435/194; 536/23.1; 536/24.3; 536/24.33
(58) Field of Search ............................... 435/91.1, 91.2, 435/194; 536/24.3, 24.33

(56) References Cited

U.S. PATENT DOCUMENTS

| | | | |
|---|---|---|---|
| 3,741,400 A | 6/1973 | Dick | 210/516 |
| 3,887,464 A | 6/1975 | Ayres | 210/117 |
| 3,945,928 A | 3/1976 | Ayres | 210/516 |
| 4,683,195 A | 7/1987 | Mullis et al. | 435/6 |
| 4,683,202 A | 7/1987 | Mullis et al. | 435/91 |
| 4,889,818 A | 12/1989 | Gelfand et al. | 435/194 |
| 4,965,188 A | 10/1990 | Mullis et al. | 435/6 |
| 5,270,171 A | 12/1993 | Cercek et al. | 435/29 |
| 5,487,973 A | 1/1996 | Nilsen et al. | 435/6 |
| 5,577,513 A | 11/1996 | Van Vlasselaer | 128/765 |
| 5,583,016 A | 12/1996 | Villeponteau et al. | 435/91.3 |
| 5,648,223 A | 7/1997 | Van Vlasselaer | 435/7.23 |
| 5,663,051 A | 9/1997 | Vlasselaer | 435/7.23 |
| 5,726,019 A | 3/1998 | Sidransky | 435/6 |
| 5,770,422 A | 6/1998 | Collins | 435/194 |
| 5,776,679 A | 7/1998 | Villeponteau et al. | 435/6 |
| 5,807,744 A | 9/1998 | Berneman et al. | 435/372 |
| 5,840,502 A | 11/1998 | Van Vlasselaer | 435/7.21 |
| 5,856,096 A * | 1/1999 | Windle et al. | 435/6 |
| 6,177,080 B1 | 1/2001 | Fleckenstein et al. | 424/186.1 |

FOREIGN PATENT DOCUMENTS

| | | |
|---|---|---|
| EP | 0566252 | 10/1993 |
| EP | 0875202 | 11/1998 |
| EP | 0566252 | 1/1999 |
| GB | 2260811 | 4/1993 |
| GB | 2317891 | 4/1998 |
| WO | 9007641 | 7/1990 |
| WO | 9601835 | 1/1996 |
| WO | 9607097 | 3/1996 |
| WO | 9718322 | 5/1997 |
| WO | 9721488 | 6/1997 |
| WO | 9802581 | 1/1998 |
| WO | 9814592 | 4/1998 |
| WO | 9822825 | 5/1998 |
| WO | 9837181 | 8/1998 |
| WO | 9859040 | 12/1998 |
| WO | 9940221 | 8/1999 |
| WO | 0046585 | 8/2000 |

OTHER PUBLICATIONS

Altschul et al., Basic Local Alignment Search Tool, *J. Mol. Biol.* 215:403–410 (1990).

BSCH Blood Transfusion Task Force: Voak, D. et al., Guidelines for the collection, processing and storage of human bone marrow and peripheral stem cells for transplantation, *Transfusion Medicine* 4:165–172 (1994).

Blasco et al., Differential regulation of telomerase activity and telomerase RNA during multi-stage tumorigenesis, *Nature Genetics* 12(2):200–204 (1996).

Borgen et al. Standardization of the immunocytochemical detection of cancer cells in BM and blood: 1. establishment of objective criteria for the evaluation of immunostained cells, *Cytotherapy* 1:377–388 (1999).

Fleming et al., A critical and comparative study of methods of isolating tumour cells from the blood, *J. Clin. Path.* 20:145–151 (1967).

Higuchi R., Recombinant PCR, *PCR Protocols: A Guide to Methods and Applications* Academic Press, Inc., pp. 177–183 (1990).

Kato et al., Isolation and Characterization of CD34+ Hematopoietic Stem Cells From Human Peripheral Blood by High-Gradient Magnetic Cell Sorting, *Cytometry* 14:384–392 (1993).

Koop et al., Fate of Melanoma Cells Entering the Microcircualtion: Over 80% Survive and Extravasate, 55:2520–2523 (1995).

(List continued on next page.)

*Primary Examiner*—Stephanie Zitomer
(74) *Attorney, Agent, or Firm*—Stephanie L. Seidman; Heller Ehrman White & McAuliffe, LLP

(57) ABSTRACT

A method for the quantification of tumor cells in a body fluid is disclosed and entails first carrying out a reaction with the sample to be investigated, in which the RNA component of telomerase is specifically amplified, and then the amount of amplified nucleic acid is determined quantitatively, as are test kits suitable therefor.

33 Claims, 11 Drawing Sheets

OTHER PUBLICATIONS

Meyerson et al., hEST2, the Putative Human Telomerase Catalytic Subunit Gene, Is Up–Regulated in Tumor Cells and during Immortalization, *Cell* 90:785–795 (1997).

Nakajima–Iijima et al., Molecular structure of the human cytoplasmic β–actin gene: Interspecies homology of sequences in the introns, *Proc. Natl. Acad. Sci. USA* 82:6133–6137 (1985).

Nakamura et al., Teomerase Catalytic Subunit Homologs from Fission Yeast and Human, *Science* 277:955–959 (1997).

Nilsen et al., Dendritic Nucleic Acid Structures, *J. Theor. Biol.* 187:273–284 (1997).

Toyonaga et al., Organization and sequences of the diversity, joining, and constant region genes of the human T–cell receptor β chain, *Proc. Natl. Acad. Sci. USA* 82:8624–8628 (1985).

Yashima et al., Telomerase activity and in situ telomerase RNA expression in malignant and non–malignant lymph nodes, *J. Clin. Pathol.* 50:110–117 (1997).

Verified English translation of International PCT application No. WO 00/46585, published Aug. 10, 2000 (item A).

Asai et al., "Telomere legnth, telomere activity and telomerase RNA expression in human esophageal cancer cells: Correlation with cell proliferation, differentiation and chemosensitivity to anticancer drugs" *Anticancer Research* 18:1465–1472 (1998).

Blasco et al., "Telomere shortening and tumor formation by mouse cells lacking telomerse RNA" *Cell* 91:25–34 (1997).

Blasco et al., "Functional characterization and developmental regulation of mouse telomerase RNA" *Science* 269:1267–70 (1995).

Boom et al., "Rapid and Simple Method for Purification of Nucleic Acids" *J. of Clin. Microbio.* 28(3):495–503 (1990).

Chadeneau et al., "Telomerase Activity Associated with Acquisition of Malignancy in Human Colorectal Cancer" *Cancer* 55:2533–2536 (1995).

Chomczynski et al., "Single–Step Method of RNA Isolation by Acid Guanidinium Thiocyanate–Phenol–Chloroform Extraction" *Analy Biochem* 162:156–159 (1987).

Counter et al., "Telomerase Activity in Normal Leukocytes and in Hematologic malignancies" *Blood* 85(9):2315–2320 (1995).

Feng et al., "The RNA Component of Human Telomerase" *Science* 269:1236–1241 (1995).

Greider et al., "A telomeric sequence in the RNA of Tetrahymena telomerase required for telomere repeat synthesis" *Nature* 337:331–337 (1989).

Guatelli et al., "Isothermal, in vitro amplification of nucleic acids by a multienzyme reaction modeled after retroviral replication" *Proc. Natl. Acad. Sci. USA* 87:1874–1878 (1990).

Higuchi et al., "A general method in vitro preparation and specific mutagensis of DNA fragments: study of protein and DNA interactions" *Nucleic Acid Research* 16(15):7351–7366 (1988).

Hiyama et al., "Alternations in telomeric repeat length in lung cancer are associated with loss of heterozygosity in p53 and Rb" *Oncogene* 10:937–944 (1995).

Kievits et al., "NASBA™ isothermal enzymatic in vitro nucleic acid amplification optimized for the diagnosis of HIV–1 infection" *J. of Virol. Meth.* 35:273–286 (1991).

Kim et al., "Specific Association of Human Telomerase Activity with Immortal Cells and Cancer" *Science* 266:2011–2015 (1994).

Kim et al., "Advanced in quanfification and characterization of telomerase activity by the telomeric repeat amplification protocol (TRAP)" *Nuc. Acids Res.* 25(13):2595–2597 (1997).

Matteucci et al., "Synthesis of Deoxyoligonucleotides on a Polymer Support" *J. Am. Chem. Soc.* 103(11):3185–3191 (1981).

Mehle et al., "Telomere Shortening in Renal Cell Carcinoma " *Cancer Res* 54:236–241 (1994).

Mueller et al., "Self–sustained sequence replication (3SR): an alternative to PCR" Histochemical *Cell Biology* 108:431–7 (1997).

Ohyashiki et al., "Telomere Shortening in Leukemic Cells in Related to their Genetic Alternations but not Replicative Capability" *Cancer Genet Cytogenet* 78:64–67 (1994).

Rogalla et al., "Two Human Breast Cancer Cell Lines Showing Decreasing Telomeric Repeat Length During Early In Vitro Passaging" *Cancer Genet Cytogenet* 77:19–25 (1994).

Sano et al., "Telomerase activity in 144 brain tumours" *Brit. J. of Cancer* 77(10):1633–1637 (1998).

Schwartz et al., "Telomerase Activity and Oncogenesis in Giant Cell Tumor of Bone" *Cancer* 75(5):1094–1099 (1995).

Shippen–Lentz et al., "Functional Evidence for an RNA Template in Telomerase" *Science* 247:546–552 (1990).

Shirotani et al., "Alternation in length of telomeric rpeats in lung cancer" *Lung Cancer* 11:29–41 (1994).

Van Gemen et al., "A one–tube quanitaive HIV–1 RNA NASBA nucleic acid amplification assay using electrochemiluminescent (ECL) labelled probes" *J. Virol. Meth.* 49:157–168 (1994).

Van Gemen et al., "Quantification of HIV–1 RNA in plasma using NASBA during HIV–1 primary infecton" *J. Virol. Meth.* 43:177–188 (1993).

* cited by examiner hTR

```
  1    GGGTTGCGGA GGGTGGGCCT GGGAGGGGTG GTGGCCATTT TTTGTCTAAC
 51    CCTAACTGAG AAGGGCGTAG CGCCGTGCT  TTTGCTCCCC GCGCGCTGTT
101    TTTCTCGCTG ACTTTCAGCG GGCGGAAAAG CCTCGGCCTG CCGCCTTCCA
151    CCGTTCATTC TAGAGCAAAC AAAAAATGTC AGCTGCTGGC CCGTTCGCCT
201    CCCGGGGACC TGCGGCGGGT CGCCTGCCCA GCCCCCGAAC CCCGCCTGGA
251    GCCGCGGTCG GCCCGGGGCT TCTCCGGAGG CACCCACTGC CACCGCGAAG
301    AGTTGGGCTC TGTCAGCCGC GGGTCTCTCG GGGCGAGGG  CGAGGTTCAC
351    CGTTTCAGGC CGCAGGAAGA GGAACGGAGC GAGTCCCGCC GCGGCGCGAT
401    TCCCTGAGCT GTGGGACGTG CACCCAGGAC TCGGCTCACA CATGCAGTTC
451    GCTTTCCTGT TGGTGGGGGG AACGCCGATC GTGCGCATCC GTCACCCCTC
501    GCCGGCAGTG GGGGCTTGTG AACCCCCAAA CCTGACTGAC TGGGCCAGTG
551    TGCTGCAAAT TGGCAGGAGA CGTGAAGGCA CCTCCAAAGT CGGCCAAAAT
601    GAATGGGCAG TGAGCCGGG  TTGCCTGGAG CCGTTCCTGC GTGGGTTCTC
651    CCGTCTTCCG CTTTTGTTG  CCTTTTATGG TTGTATTACA ACTTAGTTCC
701    TGCTCTGCAG ATTTGTTGA  GGTTTTTGCT TCTCCCAAGG TAGATCTCGA
751    CCAGTCCCTC AACGGGGTGT GGGGAGAACA GTCATTTTTT TTTGAGAGAT
801    CATTTAACAT TTAATGAATA TTTAATTAGA AGATCTAAAT GAACATTGGA
851    AATTGTGTTC CTTTAATGGT CATCGGTTTA TGCCAGAGGT TAGAAGTTTC
901    TTTTTTGAAA AATTAGACCT TGGCGATGAC CTTGAGCAGT AGGATATAAC
951    CCCCACAAGC TT
```

Fig. 1 pGEM-hTR

```
   1  GGGCGAATTG GCGGCCGCGG GTTGCGGAGG GTGGGCCTGG GAGGGGTGGT
  51  GGCCATTTTT TGTCTAACCC TAACTGAGAA GGGCGTAGGC GCCGTGCTTT
 101  TGCTCCCCGC GCGCTGTTTT TCTCGCTGAC TTTCAGCGGG CGGAAAAGCC
 151  TCGGCCTGCC GCCTTCCACC GTTCATTCTA GAGCAAACAA AAAATGTCAG
 201  CTGCTGGCCC GTTCGCCTCC CGGGGACCTG CGGCGGGTCG CCTGCCCAGC
 251  CCCCGAACCC CGCCTGGAGC CGCGGTCGGC CCGGGGCTTC TCCGGAGGCA
 301  CCCACTGCCA CCGCGAAGAG TTGGGCTCTG TCAGCCGCGG GTCTCTCGGG
 351  GGCGAGGGCG AGGTTCACCG TTTCAGGCCG CAGGAAGAGG AACGGAGCGA
 401  GTCCCGCCGC GGCGCGATTC CCTGAGCTGT GGGACGTGCA CCCAGGACTC
 451  GGCTCACACA TGCAGTTCGC TTTCCTGTTG GTGGGGGGAA CGCCGATCGT
 501  GCGCATCCGT CACCCCTCGC CGGCAGTGGG GGCTTGTGAA CCCCCAAACC
 551  TGACTGACTG GGCCAGTGTG CTGCAAATTG GCAGGAGACG TGAAGGCACC
 601  TCCAAAGTCG GCCAAAATGA ATGGGCAGTG AGCCGGGGTT GCCTGGAGCC
 651  GTTCCTGCGT GGGTTCTCCC GTCTTCCGCT TTTTGTTGCC TTTTATGGTT
 701  GTATTACAAC TTAGTTCCTG CTCTGCAGAT TTTGTTGAGG TTTTGCTTC
 751  TCCCAAGGTA GATCTCGACC AGTCCCTCAA CGGGGTGTGG GGAGAACAGT
 801  CATTTTTTT TGAGAGATCA TTTAACATTT AATGAATATT TAATTAGAAG
 851  ATCTAAATGA ACATTGGAAA TTGTGTTCCT TTAATGGTCA TCGGTTTATG
 901  CCAGAGGTTA GAAGTTTCTT TTTTGAAAAA TTAGACCTTG GCGATGACCT
 951  TGAGCAGTAG GATATAACCC CCACAAGCTT GAGTATTCTA TAGTGTCACC
1001  TAAATAGCTT GGCGTAATCA TGGTCATAGC TGTTTCCTGT GTGAAATTGT
1051  TATCCGCTCA CAATTCCACA CAACATACGA GCCGGAAGCA TAAAGTGTAA
1101  AGCCTGGGGT GCCTAATGAG TGAGCTAACT CACATTAATT GCGTTGCGCT
1151  CACTGCCCGC TTTCCAGTCG GAAACCTGT CGTGCCAGCT GCATTAATGA
1201  ATCGGCCAAC GCGCGGGGAG AGGCGGTTTG CGTATTGGGC GCTCTTCCGC
1251  TTCCTCGCTC ACTGACTCGC TGCGCTCGGT CGTTCGGCTG CGGCGAGCGG
1301  TATCAGCTCA CTCAAAGGCG GTAATACGGT TATCCACAGA ATCAGGGGAT
1351  AACGCAGGAA AGAACATGTG AGCAAAAGGC CAGCAAAAGG CCAGGAACCG
1401  TAAAAAGGCC GCGTTGCTGG CGTTTTTCCA TAGGCTCCGC CCCCCTGACG
1451  AGCATCACAA AAATCGACGC TCAAGTCAGA GGTGGCGAAA CCCGACAGGA
1501  CTATAAAGAT ACCAGGCGTT TCCCCCTGGA AGCTCCCTCG TGCGCTCTCC
1551  TGTTCCGACC CTGCCGCTTA CCGGATACCT GTCCGCCTTT CTCCCTTCGG
1601  GAAGCGTGGC GCTTTCTCAT AGCTCACGCT GTAGGTATCT CAGTTCGGTG
1651  TAGGTCGTTC GCTCCAAGCT GGGCTGTGTG CACGAACCCC CCGTTCAGCC
1701  CGACCGCTGC GCCTTATCCG GTAACTATCG TCTTGAGTCC AACCCGGTAA
1751  GACACGACTT ATCGCCACTG GCAGCAGCCA CTGGTAACAG GATTAGCAGA
1801  GCGAGGTATG TAGGCGGTGC TACAGAGTTC TTGAAGTGGT GGCCTAACTA
1851  CGGCTACACT AGAAGGACAG TATTTGGTAT CTGCGCTCTG CTGAAGCCAG
1901  TTACCTTCGG AAAAAGAGTT GGTAGCTCTT GATCCGGCAA ACAAACCACC
1951  GCTGGTAGCG GTGGTTTTTT TGTTTGCAAG CAGCAGATTA CGCGCAGAAA
2001  AAAAGGATCT CAAGAAGATC CTTTGATCTT TTCTACGGGG TCTGACGCTC
2051  AGTGGAACGA AAACTCACGT TAAGGGATTT TGGTCATGAG ATTATCAAAA
```

Fig. 5a

```
2101  AGGATCTTCA CCTAGATCCT TTTAAATTAA AAATGAAGTT TTAAATCAAT
2151  CTAAAGTATA TATGAGTAAA CTTGGTCTGA CAGTTACCAA TGCTTAATCA
2201  GTGAGGCACC TATCTCAGCG ATCTGTCTAT TTCGTTCATC CATAGTTGCC
2251  TGACTCCCCG TCGTGTAGAT AACTACGATA CGGGAGGGCT TACCATCTGG
2301  CCCCAGTGCT GCAATGATAC CGCGAGACCC ACGCTCACCG GCTCCAGATT
2351  TATCAGCAAT AAACCAGCCA GCCGGAAGGG CCGAGCGCAG AAGTGGTCCT
2401  GCAACTTTAT CCGCCTCCAT CCAGTCTATT AATTGTTGCC GGGAAGCTAG
2451  AGTAAGTAGT TCGCCAGTTA ATAGTTTGCG CAACGTTGTT GCCATTGCTA
2501  CAGGCATCGT GGTGTCACGC TCGTCGTTTG GTATGGCTTC ATTCAGCTCC
2551  GGTTCCCAAC GATCAAGGCG AGTTACATGA TCCCCATGT TGTGCAAAAA
2601  AGCGGTTAGC TCCTTCGGTC CTCCGATCGT TGTCAGAAGT AAGTTGGCCG
2651  CAGTGTTATC ACTCATGGTT ATGGCAGCAC TGCATAATTC TCTTACTGTC
2701  ATGCCATCCG TAAGATGCTT TTCTGTGACT GGTGAGTACT CAACCAAGTC
2751  ATTCTGAGAA TAGTGTATGC GGCGACCGAG TTGCTCTTGC CCGGCGTCAA
2801  TACGGGATAA TACCGCGCCA CATAGCAGAA CTTTAAAAGT GCTCATCATT
2851  GGAAAACGTT CTTCGGGGCG AAAACTCTCA AGGATCTTAC CGCTGTTGAG
2901  ATCCAGTTCG ATGTAACCCA CTCGTGCACC CAACTGATCT TCAGCATCTT
2951  TTACTTTCAC CAGCGTTTCT GGGTGAGCAA AAACAGGAAG GCAAAATGCC
3001  GCAAAAAAGG GAATAAGGGC GACACGGAAA TGTTGAATAC TCATACTCTT
3051  CCTTTTTCAA TATTATTGAA GCATTTATCA GGGTTATTGT CTCATGAGCG
3101  GATACATATT TGAATGTATT TAGAAAAATA AACAAATAGG GGTTCCGCGC
3151  ACATTTCCCC GAAAAGTGCC ACCTGACGTC TAAGAAACCA TTATTATCAT
3201  GACATTAACC TATAAAAATA GGCGTATCAC GAGGCCCTTT CGTCTCGCGC
3251  GTTTCGGTGA TGACGGTGAA AACCTCTGAC ACATGCAGCT CCCGGAGACG
3301  GTCACAGCTT GTCTGTAAGC GGATGCCGGG AGCAGACAAG CCCGTCAGGG
3351  CGCGTCAGCG GGTGTTGGCG GGTGTCGGGG CTGGCTTAAC TATGCGGCAT
3401  CAGAGCAGAT TGTACTGAGA GTGCACCATA TGCGGTGTGA AATACCGCAC
3451  AGATGCGTAA GGAGAAAATA CCGCATCAGG CGAAATTGTA AACGTTAATA
3501  TTTTGTTAAA ATTCGCGTTA AATATTTGTT AAATCAGCTC ATTTTTTAAC
3551  CAATAGGCCG AAATCGGCAA AATCCCTTAT AAATCAAAAG AATAGACCGA
3601  GATAGGGTTG AGTGTTGTTC CAGTTTGGAA CAAGAGTCCA CTATTAAAGA
3651  ACGTGGACTC CAACGTCAAA GGGCGAAAAA CCGTCTATCA GGGCGATGGC
3701  CCACTACGTG AACCATCACC CAAATCAAGT TTTTTGCGGT CGAGGTGCCG
3751  TAAAGCTCTA AATCGGAACC CTAAAGGGAG CCCCCGATTT AGAGCTTGAC
3801  GGGGAAAGCC GGCGAACGTG GCGAGAAAGG AAGGGAAGAA AGCGAAAGGA
3851  GCGGGCGCTA GGGCGCTGGC AAGTGTAGCG GTCACGCTGC GCGTAACCAC
3901  CACACCCGCC GCGCTTAATG CGCCGCTACA GGGCGCGTCC ATTCGCCATT
3951  CAGGCTGCGC AACTGTTGGG AAGGGCGATC GGTGCGGGCC TCTTCGCTAT
4001  TACGCCAGCT GGCGAAAGGG GGATGTGCTG CAAGGCGATT AAGTTGGGTA
4051  ACGCCAGGGT TTTCCCAGTC ACGACGTTGT AAAACGACGG CCAGTGAATT
4101  GTAATACGAC TCACTATA
```

Fig. 5b pGEM-hTR (Ka)

```
   1  GGGCGAATTG GCGGCCGCGG GTTGCGGAGG GTGGGCCTGG GAGGGGTGGT
  51  GGCCATTTTT TGTCTAACCC TAACTGAGAA GGGCGTAGGC GCCGTGCTTT
 101  TGCTCCCCGC GCGCTGTTTT TCTCGCTGAC TTTCAGCGGG CGGAAAAGCC
 151  TCGGCCTGCC GCCTTCCACC GTTCATTCTA GAGCAAACAA AAAATGTCAG
 201  CTGCTGGCCC GTTCGCCTCC CGGGGACCTG CGGCGGGTCG CCTGCCCAGC
 251  CCCCGAACCC CGCCTGGAGC CGCGGTCGGC CCGGGGCTTC TCCGGAGGCA
 301  CCCACTGCCA CCGCGAAGAG TTGGGCTCTG TCAGCCGCGG GTCTCTCGGG
 351  GGCGAGGGCG AGGTTCACCG TTTCAGGCCG CAGGAAGAGG AACGGAGCGA
 401  GTCCCGCCGC GGCGCGATTC CCTGAGCTGT GGGACGTGCA CCCAGGACTC
 451  GGCTCACACA TGCAGTTCGC TTTCCTGTTG GTGGGGGGAA CGCCGATCGT
 501  GCGCATCCGT CACCCCTCGC CGGCAGTGGG GGCTTGTGAA CCCCCAAACC
 551  TGACTGACTG GCCAGTGTG CTGCAAATTG GCAGatcgat gacctaagtg
 601  gatccgactt ggtaccATGA ATGGGCAGTG AGCCGGGGTT GCCTGGAGCC
 651  GTTCCTGCGT GGGTTCTCCC GTCTTCCGCT TTTTGTTGCC TTTTATGGTT
 701  GTATTACAAC TTAGTTCCTG CTCTGCAGAT TTTGTTGAGG TTTTTGCTTC
 751  TCCCAAGGTA GATCTCGACC AGTCCCTCAA CGGGGTGTGG GGAGAACAGT
 801  CATTTTTTTT TGAGAGATCA TTTAACATTT AATGAATATT TAATTAGAAG
 851  ATCTAAATGA ACATTGGAAA TTGTGTTCCT TTAATGGTCA TCGGTTTATG
 901  CCAGAGGTTA GAAGTTTCTT TTTTGAAAAA TTAGACCTTG GCGATGACCT
 951  TGAGCAGTAG GATATAACCC CCACAAGCTT GAGTATTCTA TAGTGTCACC
1001  TAAATAGCTT GGCGTAATCA TGGTCATAGC TGTTTCCTGT GTGAAATTGT
1051  TATCCGCTCA CAATTCCACA CAACATACGA GCCGGAAGCA TAAAGTGTAA
1101  AGCCTGGGGT GCCTAATGAG TGAGCTAACT CACATTAATT GCGTTGCGCT
1151  CACTGCCCGC TTTCCAGTCG GGAAACCTGT CGTGCCAGCT GCATTAATGA
1201  ATCGGCCAAC GCGCGGGGAG AGGCGGTTTG CGTATTGGGC GCTCTTCCGC
1251  TTCCTCGCTC ACTGACTCGC TGCGCTCGGT CGTTCGGCTG CGGCGAGCGG
1301  TATCAGCTCA CTCAAAGGCG GTAATACGGT TATCCACAGA ATCAGGGGAT
1351  AACGCAGGAA AGAACATGTG AGCAAAAGGC CAGCAAAAGG CCAGGAACCG
1401  TAAAAAGGCC GCGTTGCTGG CGTTTTTCCA TAGGCTCCGC CCCCCTGACG
1451  AGCATCACAA AAATCGACGC TCAAGTCAGA GGTGGCGAAA CCCGACAGGA
1501  CTATAAAGAT ACCAGGCGTT TCCCCTGGA AGCTCCCTCG TGCGCTCTCC
1551  TGTTCCGACC CTGCCGCTTA CCGGATACCT GTCCGCCTTT CTCCCTTCGG
1601  GAAGCGTGGC GCTTTCTCAT AGCTCACGCT GTAGGTATCT CAGTTCGGTG
1651  TAGGTCGTTC GCTCCAAGCT GGGCTGTGTG CACGAACCCC CCGTTCAGCC
1701  CGACCGCTGC GCCTTATCCG GTAACTATCG TCTTGAGTCC AACCCGGTAA
1751  GACACGACTT ATCGCCACTG GCAGCAGCCA CTGGTAACAG GATTAGCAGA
1801  GCGAGGTATG TAGGCGGTGC TACAGAGTTC TTGAAGTGGT GGCCTAACTA
1851  CGGCTACACT AGAAGGACAG TATTTGGTAT CTGCGCTCTG CTGAAGCCAG
1901  TTACCTTCGG AAAAAGAGTT GGTAGCTCTT GATCCGGCAA ACAAACCACC
1951  GCTGGTAGCG GTGGTTTTTT TGTTTGCAAG CAGCAGATTA CGCGCAGAAA
2001  AAAAGGATCT CAAGAAGATC CTTTGATCTT TTCTACGGGG TCTGACGCTC
2051  AGTGGAACGA AAACTCACGT TAAGGGATTT TGGTCATGAG ATTATCAAAA
```

Fig. 6a

```
2101    AGGATCTTCA CCTAGATCCT TTTAAATTAA AAATGAAGTT TTAAATCAAT
2151    CTAAAGTATA TATGAGTAAA CTTGGTCTGA CAGTTACCAA TGCTTAATCA
2201    GTGAGGCACC TATCTCAGCG ATCTGTCTAT TTCGTTCATC CATAGTTGCC
2251    TGACTCCCCG TCGTGTAGAT AACTACGATA CGGGAGGGCT TACCATCTGG
2301    CCCCAGTGCT GCAATGATAC CGCGAGACCC ACGCTCACCG GCTCCAGATT
2351    TATCAGCAAT AAACCAGCCA GCCGGAAGGG CCGAGCGCAG AAGTGGTCCT
2401    GCAACTTTAT CCGCCTCCAT CCAGTCTATT AATTGTTGCC GGGAAGCTAG
2451    AGTAAGTAGT TCGCCAGTTA ATAGTTTGCG CAACGTTGTT GCCATTGCTA
2501    CAGGCATCGT GGTGTCACGC TCGTCGTTTG GTATGGCTTC ATTCAGCTCC
2551    GGTTCCCAAC GATCAAGGCG AGTTACATGA TCCCCCATGT TGTGCAAAAA
2601    AGCGGTTAGC TCCTTCGGTC CTCCGATCGT TGTCAGAAGT AAGTTGGCCG
2651    CAGTGTTATC ACTCATGGTT ATGGCAGCAC TGCATAATTC TCTTACTGTC
2701    ATGCCATCCG TAAGATGCTT TTCTGTGACT GGTGAGTACT CAACCAAGTC
2751    ATTCTGAGAA TAGTGTATGC GGCGACCGAG TTGCTCTTGC CCGGCGTCAA
2801    TACGGGATAA TACCGCGCCA CATAGCAGAA CTTTAAAAGT GCTCATCATT
2851    GGAAAACGTT CTTCGGGGCG AAAACTCTCA AGGATCTTAC CGCTGTTGAG
2901    ATCCAGTTCG ATGTAACCCA CTCGTGCACC CAACTGATCT TCAGCATCTT
2951    TTACTTTCAC CAGCGTTTCT GGGTGAGCAA AAACAGGAAG GCAAAATGCC
3001    GCAAAAAAGG GAATAAGGGC GACACGGAAA TGTTGAATAC TCATACTCTT
3051    CCTTTTTCAA TATTATTGAA GCATTTATCA GGGTTATTGT CTCATGAGCG
3101    GATACATATT TGAATGTATT TAGAAAAATA AACAAATAGG GGTTCCGCGC
3151    ACATTTCCCC GAAAAGTGCC ACCTGACGTC TAAGAAACCA TTATTATCAT
3201    GACATTAACC TATAAAAATA GGCGTATCAC GAGGCCCTTT CGTCTCGCGC
3251    GTTTCGGTGA TGACGGTGAA AACCTCTGAC ACATGCAGCT CCCGGAGACG
3301    GTCACAGCTT GTCTGTAAGC GGATGCCGGG AGCAGACAAG CCCGTCAGGG
3351    CGCGTCAGCG GGTGTTGGCG GGTGTCGGGG CTGGCTTAAC TATGCGGCAT
3401    CAGAGCAGAT TGTACTGAGA GTGCACCATA TGCGGTGTGA AATACCGCAC
3451    AGATGCGTAA GGAGAAAATA CCGCATCAGG CGAAATTGTA ACGTTAATA
3501    TTTTGTTAAA ATTCGCGTTA AATATTTGTT AAATCAGCTC ATTTTTTAAC
3551    CAATAGGCCG AAATCGGCAA AATCCCTTAT AAATCAAAAG AATAGACCGA
3601    GATAGGGTTG AGTGTTGTTC CAGTTTGGAA CAAGAGTCCA CTATTAAAGA
3651    ACGTGGACTC CAACGTCAAA GGGCGAAAAA CCGTCTATCA GGGCGATGGC
3701    CCACTACGTG AACCATCACC CAAATCAAGT TTTTTGCGGT CGAGGTGCCG
3751    TAAAGCTCTA AATCGGAACC CTAAAGGGAG CCCCCGATTT AGAGCTTGAC
3801    GGGGAAAGCC GGCGAACGTG GCGAGAAAGG AAGGGAAGAA AGCGAAAGGA
3851    GCGGGCGCTA GGGCGCTGGC AAGTGTAGCG GTCACGCTGC GCGTAACCAC
3901    CACACCCGCC GCGCTTAATG CGCCGCTACA GGGCGCGTCC ATTCGCCATT
3951    CAGGCTGCGC AACTGTTGGG AAGGGCGATC GGTGCGGGCC TCTTCGCTAT
4001    TACGCCAGCT GGCGAAAGGG GGATGTGCTG CAAGGCGATT AAGTTGGGTA
4051    ACGCCAGGGT TTTCCCAGTC ACGACGTTGT AAAACGACGG CCAGTGAATT
4101    GTAATACGAC TCACTATA
```

Fig. 6b hTRKa

```
  1  GGGCGAAUUG GCGGCCGCGG GUUGCGGAGG GUGGGCCUGG GAGGGGUGGU
 51  GGCCAUUUUU UGUCUAACCC UAACUGAGAA GGGCGUAGGC GCCGUGCUUU
101  UGCUCCCCGC GCGCUGUUUU UCUCGCUGAC UUUCAGCGGG CGGAAAAGCC
151  UCGGCCUGCC GCCUUCCACC GUUCAUUCUA GAGCAAACAA AAAAUGUCAG
201  CUGCUGGCCC GUUCGCCUCC CGGGGACCUG CGGCGGGUCG CCUGCCCAGC
251  CCCCGAACCC CGCCUGGAGC CGCGGUCGGC CCGGGGCUUC UCCGGAGGCA
301  CCCACUGCCA CCGCGAAGAG UUGGGCUCUG UCAGCCGCGG GUCUCUCGGG
351  GGCGAGGGCG AGGUUCACCG UUUCAGGCCG CAGGAAGAGG AACGGAGCGA
401  GUCCCGCCGC GGCGCGAUUC CCUGAGCUGU GGGACGUGCA CCCAGGACUC
451  GGCUCACACA UGCAGUUCGC UUUCCUGUUG GUGGGGGAA CGCCGAUCGU
501  GCGCAUCCGU CACCCCUCGC CGGCAGUGGG GGCUUGUGAA CCCCCAAACC
551  UGACUGACUG GGCCAGUGUG CUGCAAAUUG GCAGAUCGAU GACCUAAGUG
601  GAUCCGACUU GGUACCAUGA AUGGGCAGUG AGCCGGGGUU GCCUGGAGCC
651  GUUCCUGCGU GGGUUCUCCC GUCUUCCGCU UUUUGUUGCC UUUUAUGGUU
701  GUAUUACAAC UUAGUUCCUG CUCUGCAGAU UUUGUUGAGG UUUUUUGCUUC
751  UCCCAAGGUA GAUCUCGACC AGUCCCUCAA CGGGGUGUGG GGAGAACAGU
801  CAUUUUUUUU UGAGAGAUCA UUUAACAUUU AAUGAAUAUU UAAUUAGAAG
851  AUCUAAAUGA ACAUUGGAAA UUGUGUUCCU UUAAUGGUCA UCGGUUUAUG
901  CCAGAGGUUA GAAGUUUCUU UUUUGAAAAA UUAGACCUUG GCGAUGACCU
951  UGAGCAGUAG GAUAUAACCC CCACA
```

Fig. 7 hTRKb

```
  1  GGGCGAAUUG GCGGCCGCGG GUUGCGGAGG GUGGGCCUGG GAGGGGUGGU
 51  GGCCAUUUUU UGUCUAACCC UAACUGAGAA GGGCGUAGGC GCCGUGCUUU
101  UGCUCCCCGC GCGCUGUUUU UCUCGCUGAC UUUCAGCGGG CGGAAAAGCC
151  UCGGCCUGCC GCCUUCCACC GUUCAUUCUA GAGCAAACAA AAAAUGUCAG
201  CUGCUGGCCC GUUCGCCUCC CGGGGACCUG CGGCGGGUCG CCUGCCCAGC
251  CCCCGAACCC CGCCUGGAGC CGCGGUCGGC CCGGGGCUUC UCCGGAGGCA
301  CCCACUGCCA CCGCGAAGAG UUGGGCUCUG UCAGCCGCGG GUCUCUCGGG
351  GGCGAGGGCG AGGUUCACCG UUUCAGGCCG CAGGAAGAGG AACGGAGCGA
401  GUCCGCCGC GGCGCGAUUC CCUGAGCUGU GGGACGUGCA CCCAGGACUC
451  GGCUCACACA UGCAGUUCGC UUUCCUGUUG GUGGGGGGAA CGCCGAUCGU
501  GCGCAUCCGU CACCCCUCGC CGGCAGUGGG GGCUUGUGAA CCCCCAAACC
551  UGACUGACUG GGCCAGUGUG CUGCAAAUUG GCAGAUCGAU UCCCGUCGCC
601  AAAUCGAGCG GGUACCAUGA AUGGGCAGUG AGCCGGGGUU GCCUGGAGCC
651  GUUCCUGCGU GGGUUCUCCC GUCUUCCGCU UUUUGUUGCC UUUUAUGGUU
701  GUAUUACAAC UUAGUUCCUG CUCUGCAGAU UUUGUUGAGG UUUUUUGCUUC
751  UCCCAAGGUA GAUCUCGACC AGUCCCUCAA CGGGGUGUGG GGAGAACAGU
801  CAUUUUUUUU UGAGAGAUCA UUUAACAUUU AAUGAAUAUU UAAUUAGAAG
851  AUCUAAAUGA ACAUUGGAAA UUGUGUUCCU UUAAUGGUCA UCGGUUUAUG
901  CCAGAGGUUA GAAGUUUCUU UUUUGAAAAA UUAGACCUUG GCGAUGACCU
951  UGAGCAGUAG GAUAUAACCC CCACA
```

Fig. 8 hTRKc

```
  1  GGGCGAAUUG GCGGCCGCGG GUUGCGGAGG GUGGGCCUGG GAGGGGUGGU
 51  GGCCAUUUUU UGUCUAACCC UAACUGAGAA GGGCGUAGGC GCCGUGCUUU
101  UGCUCCCCGC GCGCUGUUUU UCUCGCUGAC UUUCAGCGGG CGGAAAAGCC
151  UCGGCCUGCC GCCUUCCACC GUUCAUUCUA GAGCAAACAA AAAAUGUCAG
201  CUGCUGGCCC GUUCGCCUCC CGGGGACCUG CGGCGGGUCG CCUGCCCAGC
251  CCCCGAACCC CGCCUGGAGC CGCGGUCGGC CCGGGGCUUC UCCGGAGGCA
301  CCCACUGCCA CCGCGAAGAG UUGGGCUCUG UCAGCCGCGG GUCUCUCGGG
351  GGCGAGGGCG AGGUUCACCG UUUCAGGCCG CAGGAAGAGG AACGGAGCGA
401  GUCCCGCCGC GGCGCGAUUC CCUGAGCUGU GGGACGUGCA CCCAGGACUC
451  GGCUCACACA UGCAGUUCGC UUUCCUGUUG GUGGGGGGAA CGCCGAUCGU
501  GCGCAUCCGU CACCCCUCGC CGGCAGUGGG GGCUUGUGAA CCCCCAAACC
551  UGACUGACUG GGCCAGUGUG CUGCAAAUUG GCAGAUCGAU CGUCCAAUCG
601  CUAUACUCUC GGUACCAUGA AUGGGCAGUG AGCCGGGGUU GCCUGGAGCC
651  GUUCCUGCGU GGGUUCUCCC GUCUUCCGCU UUUUGUUGCC UUUUAUGGUU
701  GUAUUACAAC UUAGUUCCUG CUCUGCAGAU UUUGUUGAGG UUUUUGCUUC
751  UCCCAAGGUA GAUCUCGACC AGUCCCUCAA CGGGGUGUGG GGAGAACAGU
801  CAUUUUUUUU UGAGAGAUCA UUUAACAUUU AAUGAAUAUU UAAUUAGAAG
851  AUCUAAAUGA ACAUUGGAAA UUGUGUUCCU UUAAUGGUCA UCGGUUUAUG
901  CCAGAGGUUA GAAGUUUCUU UUUUGAAAAA UUAGACCUUG GCGAUGACCU
951  UGAGCAGUAG GAUAUAACCC CCACA
```

Fig. 9

METHOD OF QUANTIFYING TUMOUR CELLS IN A BODY FLUID AND A SUITABLE TEST KIT

This application is the National Stage of International Application No. PCT/DE96/02183, filed Nov. 14, 1996. Benefit of priority to 35 U.S.C. §365(b) to German application no. 195 42 795.5, filed Nov. 16, 1995 is claimed herein.

The invention relates to a method for the quantification of tumor cells in a body fluid, in which firstly a reaction is carried out with the sample to be investigated, in which reaction the RNA component of telomerase is specifically amplified, and subsequently the amount of amplified nucleic acid is determined quantitatively, and to test kits suitable therefor.

Virtually all solid malignant tumors have the potential to form metastases. The metastasis process comprises the spread of malignant cells as micrometastases, usually via the blood or lymph to remote organs and the development of autonomous secondary tumors. The extent of metastasis determines the prognosis of an oncosis.

The requirements of tumor prevention or aftercare programs are to diagnose primary tumors or a recurrence or a metastasis early, even before metastases become clinically manifest. This aim cannot yet be satisfactorily met with the available instrumental techniques; in particular, there is still a diagnostic gray zone between circulating tumor cells and incipient formation of metastases in organs. Early diagnosis of circulating malignant cells, for example in peripheral blood of a patient undergoing tumor aftercare would make it possible to apply immunomodulating therapy or polychemotherapy, which is possibly curative, at an early date, that is to say even before organ metastasis becomes manifest. Quantification of the metastases in peripheral blood before and after the therapy represents an important control in such cases.

GB 2 260 811 proposes, for example, a diagnostic method for detecting malignant tumors which are associated with normal cells of a particular body tissue, where the normal cells form at least one gene product specific for this tissue. In this detection method, body fluid, for example blood, in which the cells do not normally occur in a healthy person, is taken from the patient, and the mRNA of the specific gene product is amplified and detected. An example mentioned is tyrosinase for detecting melanoma cells in peripheral blood. However, the disadvantage of this method is that it is linked to tissue-specific gene products, does not allow quantification of the melanoma cells and, moreover, gives false-positive results.

Kim et al. describes the results of an assay with which it was possible to determine telomerase activities in tumor tissues [Kim et al. (1994). Science 266: 2011]. The telomerase activity was detected with a sensitivity of about 1 immortal cell/104 normal cells in 98 of 100 cancer cell cultures and 90 of 101 malignant tumors, and in germinal tissues, but not in 22 normal somatic cell-cultures.

Telomerase is a newly described ribonucleo-protein with reverse transcriptase activity [Shippen-Lentz et al. (1990), Science 247: 546] which uses an integral RNA sequence as template for independent DNA synthesis [Greider et al. (1989). Nature 337: 331] by which new telomeric DNA are synthesized at the ends of the chromosomes. Telomeres consist of highly conserved (TTAGGG)n in tandem sequences with a length of about 5–15 kilobases (kb)/cell genome and have the task of stabilizing the chromosomes on the nuclear membrane and protect the coding genomic DNA from uncontrolled recombination and degradation [Mehle et al. (1994). Cancer Res 54: 236]. Whereas a dynamic equilibrium between shortening of the chromosome ends and de novo synthesis of telomeric sequences by telomerase is postulated in lower eukaryotes, normal human somatic cells show low or undetectable telomerase activity. In addition, telomerase is not growth-regulated, in contrast to other DNA enzymes, since none of the actively proliferating cell cultures showed detectable telomerase activity. Only germ cells and almost all tumor cell lines [Ohyashiki et al. (1994). Cancer Genet Cytogenet 78:64; Rogalla et al. (1994). Cancer Genet Cytogenet 77: 19; Schwartz et al. (1995). Cancer 75: 1094] and tumor tissues (Lunge, [Hiyama et al. (1995). Oncogene 10: 937; Shirotani et al. (1994). Lung Cancer 11: 29], kidneys [Mehle et al. (1994). Cancer Res 54: 236], ovaries [Chadeneau et al. (1995). Cancer Res 55: 2533] and blood [Counter et al. (1995). Blood 85: 2315]) show measurable telomerase activity and a constant telomere length which is retained throughout an infinite number of cell divisions. Activation of telomerase with the stabilization, associated therewith, of the telomere length can therefore be regarded as a critical step in the direction of immortalization of somatic cells.

Feng et al. were able to clone the integral RNA sequence of human telomerase (hTR), which is encoded on the distal segment (q) of chromosome 3. The authors were able to demonstrate, by competitive polymerase chain reaction (PCR), a significant increase in telomerase expression in tumor tissues and in germinal tissues by comparison with normal somatic cells [Feng et al. (1995), Science 269: 1236]. An antisense construct of the hTR sequence caused cell death (apoptosis) in transfected HeLa cells. These data demonstrate stringent repression of telomerase in somatic tissues, as well as the fact that malignant growth depends on the presence of immortal cells and on the activation of telomerase.

The object of the present invention was therefore to develop a method with which it is possible to determine tumor cells quantitatively in a body fluid.

The invention therefore relates to a method for the quantification of tumor cells in a body fluid, in which firstly a reaction is carried out with the sample to be investigated, in which reaction the RNA component of telomerase is specifically amplified, and subsequently the amount of amplified nucleic acid is determined quantitatively, and to test kits suitable therefor. Body fluid means for the purpose of the present invention, for example, blood, urine or else stool, exudates or transudates from body cavities, especially peripheral blood.

Peripheral blood is, for example, taken from the subject by puncturing an artery, vein or finger pad and is transferred into an RNA lysis buffer which comprises, for example, urea or, preferably, guanidinium isothiocyanate, in order to denature any RNases present and to release the nucleic acids from the cells [see, for example, Chomczynski et al. (1987) Anal. Biochem. 162, 156]. The nucleic acids can be isolated from the strongly saline medium of the RNA lysis buffer, for example, by means of silica particles to which all nucleic acids are able to bind [Boom et al. (1990) J. Clin. Microbiol., 29, 495]. The particles are then washed several times with suitable buffer and the bound nucleic acids are eluted. It is subsequently advantageous to hydrolyze any genomic DNA present in the sample using RNase-free DNase in a suitable buffer, so that no false-positive results or excessive background noise result due to false amplification signals, because DNA is possibly still present, in the later amplification of the RNA components of telomerase. This is generally followed by inactivation of the DNase, for example by phenol extraction and/or heat denaturation. It is possible and advantageous, before or, preferably, after treatment of the sample with DNase, also to purify the RNA present in the sample further, for example by chromatographic methods such as ion exchange chromatography, preferably on silica gel.

To check whether possibly interfering genomic DNA is still present in the sample, it is subsequently possible to carry out an amplification reaction with the telomerase-specific oligonucleotide primers which are described hereinafter, in which case the RNA present in the sample is not transcribed to cDNA by a reverse transcription reaction beforehand. Only in the case where the sample is free of telomerase-specific DNA does no amplification take place, with the result that no amplified DNA can be measured.

This is followed by transcription of the RNA present in the sample into cDNA, generally by means of the reverse transcription reaction, for example with AMV reverse transcriptase. The method is generally known and is described, for example, in Sambrook et al., Molecular Cloning: A Laboratory Manual, New York Cold Spring Harbor Laboratory, 1989. In a preferred embodiment of the reverse transcription, it is also possible to use a thermostable RNA-dependent DNA polymerase as described in WO 90/07641. Suitable oligonucleotide primers for the reverse transcriptase are, for example and advantageously, the oligonucleotide primers described below or random primers with a particular length.

The subsequent amplification can be carried out, for example, with a DNA polymerase, for example by the polymerase chain reaction (PCR) (see, for example, U.S. Pat. Nos. 4,683,195; 4,683,202; 4,965,188) or, preferably, with an RNA polymerase by, for example, isothermal nucleic acid sequence-based amplification (NASBA). Specific oligonucleotide primers derived from the nucleic acid to be amplified are required for the amplification in each case. It is possible in the present invention to use any sequence section of the RNA component of telomerase for synthesizing the oligonucleotide primers. The oligonucleotide primers are preferably about 20 to about 30, preferably about 20 to about 25, nucleotides long. The amplification product is generally about 100 to about 2000 bases, preferably about 200 to about 1500 bases, in particular about 300 to about 350 bases, long. The following oligonucleotide primers, which have been derived from the sequence shown in FIG. 1, are particularly preferred for the novel method:

5' GACTCGGCTC ACACATGCAG TTCGC 3' (TM1) (SEQ ID NO:1), and/or

5' CTGGTCGAGA TCTACCTTGG GAGAAGC 3' (TM2) (SEQ ID NO:2), where TM1 and/or TM2 may, where appropriate, additionally comprise a promoter sequence for an RNA polymerase. The oligonucleotide primer TM1 corresponds to the 5' primer and TM2 corresponds to the 3' primer. The amplification product is 327 bp long. The primers may, for example, be prepared synthetically using the triester methods [Matteucci et al., (1981), J. Am. Chem. Soc., 103, 3185–3191]. The DNA polymerase which can be used is, for example, a non-thermostable DNA polymerase such as T4 DNA polymerase, T7 DNA polymerase, *E. coli* polymerase I or the Klenow fragment of *E. coli* or, preferably, a thermostable DNA polymerase such as Taq polymerase (see, for example, U.S. Pat. No. 4,889,818).

The general principle of the PCR consists of heat-denaturation of the DNA and restoration of the double strand in the presence of suitable oligonucleotide primers with opposite orientation of the single strand using DNA polymerase in several repeated reaction cycles. The cycle is then repeated until sufficient DNA has been formed for quantification by one of the methods described below. In general, about 20 to about 40 cycles, preferably about 30 to about 35 cycles, suffice.

In the NASBA method (also called 3SR system) there is use of at least one oligonucleotide primer, preferably TM2, which comprises a promoter for the RNA polymerase, preferably for T7 RNA polymerase [see, for example, Guatelli et al. (1990) Proc. Natl. Acad. Sci. USA, 87, 1874–1878 or Kievits et al. (1991), J. Virol. Methods, 35, 273–286]. Firstly, as already described in detail above, the RNA is transcribed with the aid of one of the oligonucleotide primers described above and of a reverse transcriptase, preferably AMV reverse transcriptase, into cDNA. The reaction product is an RNA:DNA double strand whose RNA component is then degraded by an RNase, preferably RNase H, to give a DNA single strand. Using one of the oligonucleotide primers described above, the DNA single strand is made up to the DNA double strand using a DNA polymerase. AMV reverse transcriptase is once again a suitable and preferred DNA polymerase because this transcriptase has not only an RNA-dependent DNA polymerase activity but also a DNA-dependent DNA polymerase activity. The reaction product is a DNA double strand which comprises the promoter for, for example, T7 RNA polymerase. The RNA polymerase then synthesizes an "antisense" RNA strand again, and the cycle can begin again. In general, about 20 to about 40 cycles, preferably about 30 to about 35 cycles, suffice to provide sufficient amplification product, preferably "antisense" RNA, for the subsequent quantification.

The amplification products can be quantified by, for example, staining them with ethidium bromide and detecting and quantifying them directly, for example, in an agarose or polyacrylamide gel. However, it is advantageous for the amplification products to be labeled already during the amplification, because this achieves higher sensitivity. Examples of suitable labels are radioactive labels, biotin labels, fluorescent or electrochemoluminescent (ECL) labels. The labels are, as a rule, carried by the nucleotides as starting materials for amplification by DNA or RNA polymerase. The radiolabeled amplification products (for example PCR or NASBA products) can be detected by measuring the radioactivity, the biotin-labeled amplification products can be detected via a dye which carries avidin or streptavidin, the fluorescent-labeled amplification products can be detected with a fluorometer and the electrochemoluminescent-labeled amplification products can be detected with an ECL detector. However, the most preferred detection method is in vitro hybridization with a previously labeled oligonucleotide which is complementary to the amplification product. The oligonucleotide generally carries the labels described above, and in connection with the NASBA amplification method the hybridization probe carries an electrochemoluminescent label, preferably a tris [2,2-bipyridine]ruthenium[II] complex label [see, for example, van Gemen et al. (1994), J. Virol. Methods, 49, 157–168].

Accurate and sensitive quantification of the amplification products can advantageously be achieved by coamplification of a defined amount of one or more known nucleic acids (standard nucleic acids) [see, for example, van Gemen et al. (1993), J. Virol. Methods, 43, 177–188]. In this case, a different but exactly known amount of the coamplifying standard nucleic acid or nucleic acids is added, for example in the form of a dilution series, to the unknown amounts of the sample to be investigated, and the amplification products of the sample and one or more coamplifying standard nucleic acids are determined quantitatively in independent mixtures. Comparison of the measured results reveals the amount of the RNA component of telomerase to be determined in the sample.

It is advantageous to amplify the coamplifying standard nucleic acid or nucleic acids with the same oligonucleotide primer as the sample to be investigated and the amplification products also have essentially the same length. It is particularly preferred for the coamplifying nucleic acids to have the same sequence as the amplification product of the sample to be determined, with the exception of about 20 nucleic acids between the oligonucleotide primer binding sites, which have an arbitrary but known sequence. It is possible thereby to quantify, independently of one another, the amplification product to be determined in the sample from the coamplifying amplification product, for example by a hybridization as described in detail, for example, in Sambrook et al. (supra), using appropriately complementary labeled oligonucleotides. It is particularly advantageous if several, preferably three, different coamplifying nucleic acids are added in different concentrations to the sample, because this makes it possible to reduce the number of individual amplification reactions which would otherwise have to be carried out [see van Gemen et al. (1994) J. Virol. Methods 49, 157–168]. It is also particularly preferred to add the coamplifying nucleic acids to the RNA lysis buffer described above because it is possible thereby to exclude the effect of possible nucleic acid losses in the subsequent workup of the sample.

Suitable and advantageous coamplifying standard nucleic acids in the present invention are RNA single stranded sequences which are prepared by in vitro transcription, for example with Sp6 or T7 RNA polymerase, from constructs which comprise the DNA or cDNA of the sample to be amplified and which are in each case provided with a randomized exchange of a sequence of, for example, about 10 to about 30, preferably about 20, nucleotides.

The constructs preferably consist of a transcription vector having a binding site for Sp6 or T7 RNA polymerase between a "multiple cloning site" in which the DNA or cDNA of the sample to be amplified has been cloned. The cloned sequence can be opened by selective hydrolysis with restriction endonucleases, preferably with two different restriction endonucleases, and a fragment of a defined length can be cut out and replaced by a fragment of equal length, for example using T4 ligase. The cloned fragment may comprise replacement of a sequence of any length, for example about 10 to about 30, preferably about 20, nucleic acids and is preferably located between the oligonucleotide primer binding sites. This procedure can be repeated in order to insert other nucleic acid sequences at the same site. If no suitable cleavage sites can be found, for example because the vector is also cut, it is necessary to create artificial cleavage sites. This can take place, for example, by recombinant PCR which is described in essence by Higuchi et al. [Higuchi, R. (1988). Nucleic Acid Res 16: 7351–7367; Higuchi, R. (1990). M. Innis A. et al. eds. San Diego, New York, Berkley, Boston, London, Sydney, Tokyo, Toronto, Academic Press, Inc. 177–183] and in the experimental part of the present invention.

Preferably used for the purpose of the invention are in vitro transcribed RNA single stranded sequences of constructs which a) comprise the entire cDNA of the RNA component of human telomerase and b) in which a randomized exchange of a sequence of about 20 nucleotides has been introduced.

The constructs are derived from the constructs pGEM-hTR shown in FIGS. 5a and 5b (SEQ ID NO:17)

pGEM-hTR(Ka) shown in FIGS. 6a and 6b (SEQ ID NO:18).

It is possible by in vitro transcription of the constructs with Sp6 RNA polymerase to prepare standard RNA nucleic acids which are individually 975 base pairs long and have the sequence:

(hTRKa) shown in FIG. 7 (SEQ ID NO:19)

(hTRKb) shown in FIG. 8 (SEQ ID NO:20)

(htRKc) shown in FIG. 9 (SEQ ID NO:21).

The randomized sequence in which the standard nucleic acids differ from the wild-type RNA is in this example located in position 591–610 shown in FIG. 5a. It is 20 base pairs long.

Since the standard nucleic acids differ from one another and from the wild-type sequence in this example only by a randomized and known sequence which is 20 base pairs long, the amplification products of the standard nucleic acids and of the wild-type sequence can be detected by complementary binding of labeled oligonucleotides in four separate mixtures. Oligonucleotides which are particularly suitable for specific detection of the amplified cDNA of the RNA component of telomerase (wt) and of the standard nucleic acids (hTRKa), (hTRKb) and (hTRKc) according to the present invention are the following sequences, which have been derived from the sequences shown in FIGS. 7–9:

```
5'CGACTTTGGA GGTGCCTTCA 3'   O(wt)    (SEQ ID NO:3)

5'AAGTCGGATC CACTTAGGTC 3'   O(Ka)    (SEQ ID NO:4)

5'CGCTCGATTT GGCGACGGGA 3'   O(Kb)    (SEQ ID NO:5)

5'GAGACTATAG CGATTGGACG 3'   O(Kc)    (SEQ ID NO:6).
```

The corresponding reverse complementary sequences are used to detect the amplified "antisense" RNA.

After this, the individual amplified amounts of wild-type and standard nucleic acids are determined. The unknown initial amount of the wild-type sequence can be calculated by comparing with the different amplified amounts of the standard nucleic acids when the initial amount is known (for example hTRKa: $10^2$, hTRKb: $10^4$ and hTRKc: $10^6$ molecules). It is then possible to conclude from this the number of metastases for the removed body fluid.

As internal positive control of the method and of the sample to be investigated it is possible additionally to amplify and detect a nucleic acid which generally always occurs in a body fluid. Examples of suitable nucleic acids are the mRNA coding for β-globin or for glyceraldehyde-phosphate dehydrogenase (GAPDH) (see, for example, GB 2 260 811) which always occur in the cells of the body fluid. Suitable oligonucleotide primers for human β-globin mRNA are, for example, primers with the sequences:

```
5'ACCCAGAGGT TCTTTGAGTC 3' and    (SEQ ID NO:7)

5'TCTGATAGGC AGCCTGCACT 3'        (SEQ ID NO:8),
``` where the oligonucleotide primers may, where appropriate, additionally comprise a promoter sequence for an RNA polymerase.

To prevent or reduce false-positive results or so-called background noise which is caused by telomerase activities which are possibly present in nontumor cells, it is advantageous to purify the body fluid which has been taken before the novel investigation. The intention is, in particular, to deplete stem cells and/or activated immune cells, or concentrate tumor cells, in the sample to be investigated. Since, as a rule, the individual cells have specific surface markers, removal or concentration of the cells by immunoabsorption is particularly advantageous. Examples of suitable methods are magnetic (MACS) or fluorescence-activated (FACS) cell sortings [see, for example, Göttlinger & Radbruch (1993) mta, 8, 530–536, No. 5]. Thus, for example, hemopoietic stem cells can be removed from the blood sample by means of MACS via their CD34 surface marker [Kato & Radbruch (1993) Cytometry, 14, 384–392]. B cells can be removed, for example, via their CD10, CD19 and/or CD20 surface markers, and T cells via CD45RA and/or CD7. Tumor cells can be concentrated via their specific tumor markers, for example CEA. Besides MACS or FACS, also particularly suitable for depletion or concentration of the relevant cells are antibodies against the specific surface markers, which are bound in particular to commercially obtainable magnetic beads (for example Dynabeads M450, Dynal Corp.).

It is also particularly advantageous, alone or in conjunction with the purification methods described above, to compare the amount of RNA component of telomerase from venous blood with the amount of RNA component of telomerase from arterial blood, since it is possible to detect, for the purpose of tumor cell determination, only about 20% of all cells in venous blood samples, compared with 100% of the cells in arterial blood samples [Koop, S. et al. (1995) Cancer Res. 55, 2520–2523]. It is likewise suitable to compare blood from the finger pad with venous or arterial blood.

Quantitative determination of the RNA component of telomerase in the sample makes it possible to determine whether tumor cells, especially metastases, in particular micrometastases, of malignant tumors are present in the body fluid, and in what quantity. This is of great use in particular for early clinical diagnosis of the formation of metastases from malignant tumors and for monitoring tumor therapy. Tumor cells which can be detected with the present invention are, in particular, tumor cells from metastases, preferably micrometastases, from malignant tumors, especially cells from metastasizing tumors and/or neoplasms which are derived, for example, from a T-cell lymphoblastoma, T-cell leukemia cells, chronic myeloid leukemia cells, acute lymphatic leukemia cells, chronic lymphatic leukemia cells, teratocarcinoma, melanoma, carcinoma of the lung, large bowel cancer, breast cancer, hepatocellular carcinoma, kidney tumor, adrenal tumor, prostate carcinoma, neuroblastoma, brain tumor, small-cell carcinoma of the lung, rhabdomyosarcoma, leiomyosarcoma and/or lymphoma.

The present invention further relates to the oligonucleotide primers with the sequence

```
5' GACTCGGCTC ACACATGCAG TTCGC 3' (TM1)                         (SEQ ID NO:1),

5' CTGGTCGAGA TCTACCTTGG GAGAAGC 3' (TM2)                       (SEQ ID NO:2),

5' ATAAGAATGC GGCCGCGGGT TGCGGAGGGT GGGCCTGGGA GGG 3' (TMK1)    (SEQ ID NO:9),

5' CCCAAGCTTG TGGGGGTTAT ATCCTA 3' (TMK2)                       (SEQ ID NO:10),

5' CGCGGATCCA CTTAGGTCAT CGATCTGCCA ATTTGCAGCA CACT 3' (TMK3)   (SEQ ID NO:11)

and/or

5' CGCGGATCCG ACTTGGTACC ATGAATGGGC AGTGAGCCGG 3' (TMK4)        (SEQ ID NO:12),
``` where TM1 and/or TM2 may, where appropriate, additionally comprise a promoter sequence for an RNA polymerase; and an oligonucleotide with the sequence

```
5' CCATCGATTC CGTCGCCAA ATCGAGCGGG TACCCC 3' (Kb)   (SEQ ID NO:13)

3' GGTAGCTAAG GGCAGCGGTT TAGCTCGCCC ATGGGG 5', or

5' CCATCGATCG TCCAATCGCT ATACTCTCGG TACCCC 3' (Kc)  (SEQ ID NO:14)

3' GGTAGCTAGC AGGTTAGCGA TATGAGAGCC ATGGGG 5';
``` and
a nucleic acid construct pGEM-hTR as shown in FIGS. 5a and 5b or a nucleic acid construct pGEM-hTR(Ka) as shown in FIGS. 6a and 6b;
and the standard RNA nucleic acid for coamplification of the sequence:
  (hTRKa) as shown in FIG. 7 (SEQ ID NO:19)
  (hTRKb) as shown in FIG. 8 (SEQ ID NO:20)
  (hTRKc) as shown in FIG. 9 (SEQ ID NO:21), and the cDNAs thereof, and the oligonucleotides for detecting the amplified cDNA of the wild-type nucleic acid and of the cDNA of the hTRKa, hTRKb and hTRKc standard nucleic acids with the sequence:

```
5' CGACTTTGGA GGTGCCTTCA 3'  O(wt)  (SEQ ID NO:3)

5' AAGTCGGATC CACTTAGGTC 3'  O(Ka)  (SEQ ID NO:4)

5' CGCTCGATTT GGCGACGGGA 3'  O(Kb)  (SEQ ID NO:5)

5' GAGAGTATAG CGATTGGACG 3'  O(Kc)  (SEQ ID NO:6)
``` and the corresponding reverse complementary sequences of the oligonucleotides for detecting the amplified "antisense" RNA.

The invention additionally relates to a kit for quantifying tumor cells in a body fluid, for example blood, urine or else stool, exudates or transudates from body cavities, especially peripheral blood, comprising (a) nucleic acid or nucleic acids for the coamplification, and (b) oligonucleotide primer pair for specific amplification of telomerase-encoding nucleic acid and of the nucleic acid or nucleic acids specified in (a), where the standard RNA nucleic acid for the coamplification mentioned in (A) has or have the following sequence:

(hTRKa) as shown in FIG. 7 (SEQ ID NO:19)

(hTRKb) as shown in FIG. 8 (SEQ ID NO:20)

(hTRKc) as shown in FIG. 9 (SEQ ID NO:21), and/or the oligonucleotide primer pair preferably the following sequences:

```
5' GACTCGGCTC ACACATGCAG TTCGC 3' (TM1) and/or    (SEQ ID NO:1)

5' CTGGTCGAGA TCTACCTTGG GAGAAGC 3' (TM2)          (SEQ ID NO:2),
``` where TM1 and/or TM2 may, where appropriate, additionally comprise a promoter sequence for an RNA polymerase.

The novel kit may also comprise in addition, as described in detail above, a labeled oligonucleotide as hybridization probe for specific detection of the amplified cDNA of the wild-type sequence and/or several labeled oligonucleotides as hybridization probe for specific detection of the amplified cDNA of the standard nucleic acid or nucleic acids. In addition, a novel kit for PCR amplification may additionally comprise the enzymes described in detail above, where appropriate labeled nucleotides and/or suitable buffers, such as, for example, a reverse transcriptase, preferably an AMV reverse transcriptase, a DNA polymerase, preferably a Taq polymerase and/or a DNase and, where appropriate, means suitable for depletion of stem cells and/or activated immune cells and/or for concentration of tumor cells, as described in detail above.

Another novel kit for NASBA may likewise comprise, besides the standard nucleic acids described in detail above, a labeled oligonucleotide as hybridization probe for specific detection of the amplified "antisense" RNA of the wild-type sequence and/or several labeled oligonucleotides as hybridization probe for specific detection of the amplified "antisense" RNA of the standard nucleic acid or nucleic acids. It may additionally likewise comprise the enzymes described in detail above, where appropriate labeled nucleotides and/or suitable buffers, such as, for example, a reverse transcriptase, preferably an AMV reverse transcriptase, an RNA polymerase, preferably a T7 RNA polymerase, an RNase H and/or a DNase, and, where appropriate, means suitable for depletion of stem cells and/or activated immune cells and/or for concentration of tumor cells, as described in detail above.

The following examples and figures are intended to describe the present invention in detail without, however, restricting it thereto.

DESCRIPTION OF THE FIGURES

FIG. 1 (SEQ ID NO:16) shows the RNA component of human telomerase and the position of the designed oligonucleotide primers: 5' primer TM1 (position 428–452) and 3' primer TM2 (position 728–754) with an amplification product of 327 base pairs (bp) or 5' primer TMK1 ([16 bp]+1–27) and 3' primer TMK2 (position 940–962+[3 bp]) with an amplification product of 981 bp. Hydrolysis with the restriction endonucleases NotI and HindIII give the 962 bp fragment hTR.

Bands 1: MT4, T-cell lymphoblastoma cell line, bands 2: C8166, T-cell leukemia cell line, bands 3: K562, chronic myeloid leukemia (CML) cell line, bands 4: Molt4, acute lymphatic leukemia (ALL) cell line and bands 5: teratocarcinoma cell line; M: 100 bp marker. hTR: RT-PCR with the TM1 and TM2 primers; hTR/φRT: control PCR without reverse transcription (RT) reaction, GAPDH: control RT-PCR with primers for glyceraldehyde-phosphate dehydrogenase (GAPDH).

Figure 3:
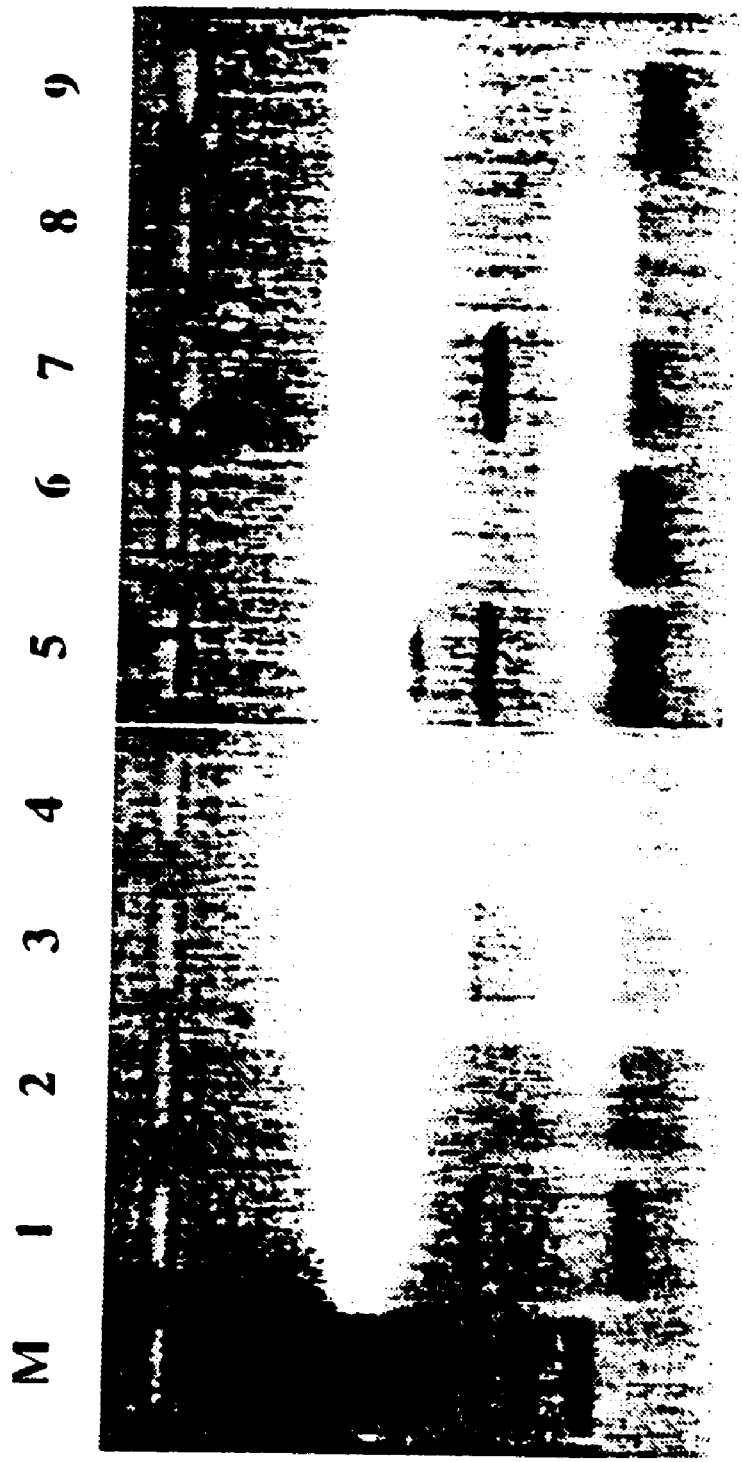

FIG. 3 shows a PCR amplification with the TM1 and TM2 primers on the cDNA from tumor tissues and healthy reference tissues. M: 100 bp marker; band 1: kidney carcinoma, band 2: healthy kidney tissue; band 3: thyroid carcinoma, band 4: healthy thyroid tissue, band 5: carcinoma of breast, band 6: healthy breast tissue; band 7: colon carcinoma, band 8: healthy large bowel tissue; band 9: H$_2$O control reaction.

Figure 4:
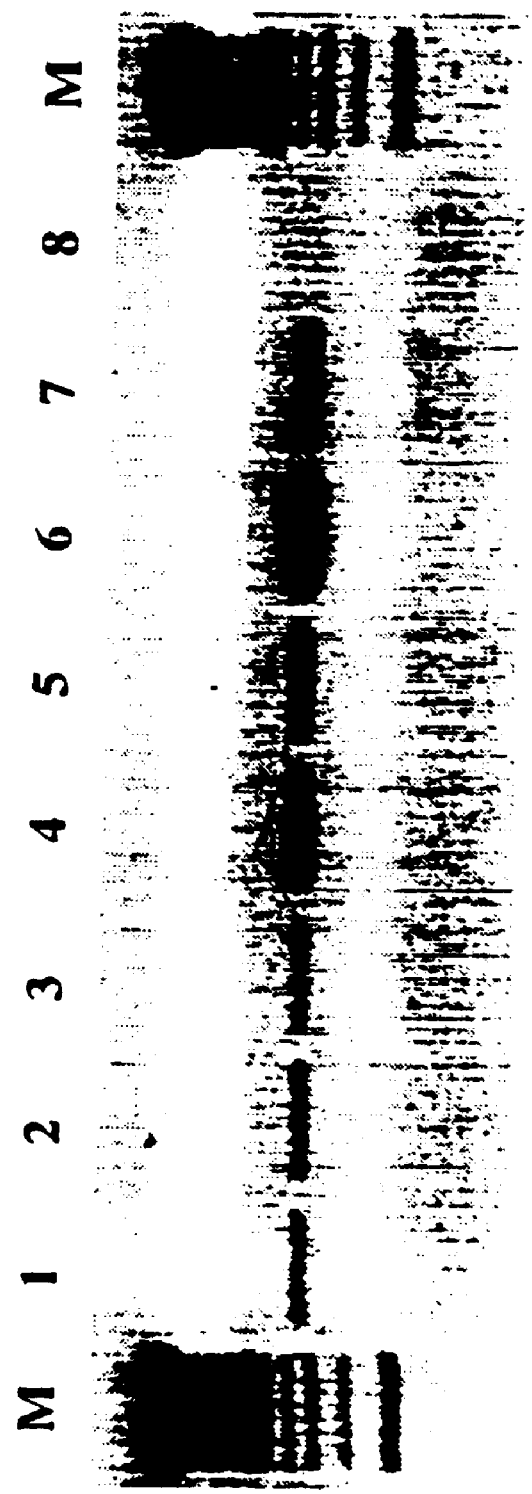

FIG. 4 shows a PCR amplification with the TM1 and TM2 primers on the cDNA from peripheral blood of normal subjects and leukemia patients. M: 100 bp marker; bands 1–3: healthy blood donors; bands 4–8: patients with acute myeloid leukemia (AML); band 9: H$_2$O control reaction.

FIGS. 5*a* and 5*b* (SEQ ID NO:17) show the construct pGEM-hTR (4118 bp) with the transcription vector pGEM-13Zf(+) and the fragment hTR(NotI/HindIII) shown in FIG. 1, which comprises the cDNA of the RNA component of human telomerase (bases 1–956: position 12–975). The position of the NotI addition (position: 12–17) by the oligonucleotide primer TMK1 is shown by dotted line.

FIGS. 6*a* and 6*b* (SEQ ID NO:18) show the construct pGEM-hTR(Ka) (4118 bp) with the ClaI-BamHI-KpnI cassette (position: 585–616) and the positions of the designed oligonucleotide primers (5' primer TMK1: position [16 bp]+1–27, 3' primer TMK3: position 565–605+[24 bp]) with an amplification product of 606 bp, (5' primer TMK4: position 60–636+[20 bp], 3' primer TMK2: position 940–962+[3 bp]) with an amplification product of 387 bp. Hydrolysis with the restriction endonucleases NotI and BamHI or BamHI and HindIII gives a product of 588 or 375 bp respectively. Ligation of the fragments in pGEM-13Zf(+) gives a product of 963 bp.

FIG. 7 (SEQ ID NO:19) shows the standard RNA hTRKa (975 bp) after in vitro transcription with Sp6 RNA polymerase on the construct pGEM-hTRKa, which has been linearized with HindIII, and the position of the randomized sequence of 20 bp (position 591–610).

FIG. 8 (SEQ ID NO:20) shows the standard RNA hTRKb (975 bp) after in vitro transcription with Sp6 RNA polymerase on the construct pGEM-hTRKb, which has been linearized with HindIII, and the position of the randomized sequence of 20 bp (position 591–610).

FIG. 9 (SEQ ID NO:21) shows the standard RNA hTRKc (975 bp) after in vitro transcription with Sp6 RNA polymerase on the construct pGEM-hTRKc, which has been linearized with HindIII, and the position of the randomized sequence of 20 bp (position 591–610).

EXAMPLES

Unless noted otherwise, the following examples were carried out by standard methods as described, for example, by Sambrook, J. et al. (1989) supra, or in accordance with the instructions of the manufacturers of the kits and enzymes used.

1. Cultivation and isolation of peripheral blood, tissue and cells

Tumor cell lines such as MT4 (T-cell lymphoblastoma), C8166 (T-cell leukemia), K562 (chronic myeloid leukemia (CML)), Molt4 (acute lymphatic leukemia (ALL)) and teratocarcinoma were cultured as recommended by the ATCC (American Tissue Culture Collection). Venous blood donated by leukemia patients (acute myeloid leukemia) and healthy control subjects was taken by puncture of a forearm vein in EDTA-monovets® (Saarsted). Human tumor tissue and healthy reference tissue were shock-frozen immediately after removal in liquid nitrogen and stored at −70° C.

2. Isolation of cellular RNA

Total cellular RNA was isolated by standard methods [Chomczynski et al. (1987) Anal Biochem 162, 156; Sambrook, J. et al. (1989). Cold Spring Harbor, N.Y., USA, Cold Spring Harbor Laboratory Press]. Peripheral blood was transferred immediately after removal into RNA lysis buffer (4 M guanidinium isothiocyanate; 0.1 M Tris-HCl, pH 7.5; 1% mercaptoethanol). Tissues and cells were homogenized in RNA lysis buffer using an Ultra-Turrax T25 dispersing apparatus (Laborreaktor-Systeme, IKA). The mixtures were either immediately processed further or stored at −70° C.

3. Reverse transcription and polymerase chain reaction (RT-PCR)

The RT-PCR was carried out with the GeneAmp® RNA-PCR kit (Perkin Elmer) as specified by the manufacturer. Aliquots of the isolated total RNA from peripheral blood, cell lines and tissues were in each case previously hydrolyzed with 20 U of DNase (Boehringer, Mannheim) in 10 µl mixtures (in 50 mM KCl; 10 mM Tris-HCl, pH 8.3 and 2.5 mM $MgCl_2$) at 37° C. for 60 minutes and then the DNase was inactivated at 95° C. for 30 minutes. For complete purification of the RNA from proteins and DNA fragments, the DNase hydrolysates were in each case purified again on a silica gel matrix (RNeasy®, Qiagen) and measured by photometry.

The two oligonucleotide primers:
TM1 5' GACTCGGCTC ACACATGCAG TTCGC 3' (SEQ ID NO:1)
TM2 5' CTGGTCGAGA TCTACCTTGG GAGAAGC 3' (SEQ ID NO:2) were designed in accordance with the sequence, published by Feng et al., of the RNA component of human telomerase (Feng, J. et al. (1995). Science 269: 1236–41) (FIG. 1) and synthesized using an Applied Biosystems 380A synthesizer. The specificity of the TM1 and TM2 primers was checked by computer-assisted analysis of homology on the nucleic acid sequences in the GenBank, EMBL, DDBJ and PDB databanks using BLASTN 1.4.9 MP [Altschul, S. F. et al. (1990). J Mol Biol 215: 403–410].

For consistency of the amplified amounts, the same amounts of RNA were employed for the RT reaction in each experiment. In order to preclude contamination of the RNA preparations with genomic DNA, each RNA-containing sample hydrolyzed with DNase was first subjected to the PCR described below and checked for amplification. The RNA-containing sample in which no amplification product was detectable was employed for the subsequent cDNA synthesis and PCR steps. Oligonucleotide primers for GAPDH were employed as internal standard control.

The PCR was carried out on 5 µl of the cDNA reaction or on a 1:50 dilution of the isolated plasmid DNA in accordance with the following program: (95° C.: 2 minutes, preheating); (94° C.: 30 seconds, 60° C.: 30 seconds, 72° C.: 30 seconds, 35 cycles); (72° C.: 7 minutes, final extension). The amplification products were fractionated by gel electrophoresis on 1.5% TAE agarose gel, stained with ethidium bromide and visualized and recorded by photography under UV light (see FIGS. 2–4).

4. Preparation of the standard RNA nucleic acids hTRKa, hTRKb and hTRKc

The enzymes used, such as Sp6 RNA polymerase, T4 ligase and restriction endonucleases, inter alia from Boehringer Mannheim, Biolabs and Promega, were used as recommended by the manufacturers. The PCR amplification products intended for cloning were fractionated by gel electrophoresis on 1.5% TAE agarose and eluted (Qiagen). The restriction hydrolysates were purified by phenol/chloroform extraction and precipitated in salt and ethanol or by DNA purification (Qiagen). The constructs were cloned by ligating the fragments into the corresponding cleavage sites in the cloning and transcription vector pGEM-13Zf(+) using T4 ligase. This vector permits in vitro transcription of cloned fragments by use of Sp6 or T7 RNA polymerases as selected. Competent bacteria (XL-1Blue, Stratagene) were transformed by electroporation (BioRad). Plasmid DNA was purified using plasmid purification kits (Qiagen). Positive clones were validated using vector- or sequence-specific oligonucleotide primers with the PCR. Sequence validation was carried out for the constructs by semiautomatic sequence analysis.

The construct pGEM-hTR (FIGS. 5a and 5b) was created as initial construct for the constructs pGEM-hTR(Ka) (FIGS. 6a and 6b), pGEM-hTR(Kb) and pGEM-hTR(Kc). pGEM-hTR(Ka) differs from pGEM-hTR by a randomized exchange of sequence in position 585–616. The constructs pGEM-hTRKb and pGEM-hTRKc differ from pGEM-hTR by a randomized sequence exchange in position 587–615. The constructs were used for in vitro transcription with Sp6 RNA polymerase of the standard RNA: hTRKa (FIG. 7), hTRKb (FIG. 8) and hTRKc (FIG. 9). To form the construct pGEM-hTR, the cDNA of the RNA component of human telomerase hTR (FIG. 1) was cloned into the NotI and HindIII cleavage sites of pGEM-13Zf(+). This was achieved by carrying out an RT-PCR with the following oligonucleotide primers, which were derived from the sequence hTR (FIG. 1),

```
5' ATAAGAATGC GGCCGCGGGT TGCGGAGGGT GGGCCTGGGA GGG 3'  (TMK1)  (SEQ ID NO:9)

5' CCCAAGCTTG TGGGGGTTAT ATCCTA 3'  (TMK2)              (SEQ ID NO:10)
``` on the previously isolated RNA from tumor cells or lines under the conditions described above. The oligonucleotide primer TMK1 (position 1–27, FIG. 1) contains an additional 5' extension of 16 bp and a NotI cleavage site, and the oligonucleotide primer TMK2 (position 940–962, FIG. 1) contains an additional 3 bp extension and a HindIII cleavage site. The TMK1 and TMK2 primer pair amplifies a 979 bp fragment. After a restriction hydrolysis with NotI and HindIII, the 963 bp fragment hTR(NotI-HindIII) (position 1–957, FIG. 5) was cloned into the corresponding cleavage sites (position 12 and 38) of pGEM-13Zf(+), and the 4118 bp construct pGEM-hTR was created. pGEM-hTR(Ka) was constructed by replacing a 32 bp sequence in the construct pGEM-hTR (position 585–616) by a 32 bp ClaI-BamHI-KpnI cassette:

```
5' ATCGATGACC TAAGTGGATC CGACTTGGTA CC 3'    (SEQ ID NO:15)

3' TAGCTACTGG ATTCACCTAG GCTGAACCAT GG 5'.
```

This replacement was carried out by recombinant PCR and is a modification of the method described by Higuchi et al. [Higuchi, R. (1988). Nucleic Acid Res 16: 7351–7367; Higuchi, R. (1990). M. Innis A. et al. eds. San Diego, New York, Berkley, Boston, London, Sydney, Tokyo, Toronto, Academic Press, Inc. 177–183]. In a first step, two independent PCRs were carried out on pGEM-hTR:

The $1^{st}$ PCR took place with the following oligonucleotide primers, which were derived from the sequence hTR (FIG. 1):

```
5' ATAAGAATGC GGCCGCGGGT TGCGGAGGGT GGGCCTGGGA GGG 3' (TMK1)(SEQ ID NO:9

5' CGCGGATCCA CTTAGGTCAT CGATCTGCCA ATTTGCAGCA CACT 3'    (SEQ ID NO:11)
   (TMK3)
```

The oligonucleotide primer TMK3 (position 565–605, FIG. 6) contains an additional 5' extension of 24 bp with a BamHI and ClaI cleavage site and encodes 21 bp of the ClaI-BamHI-KpnI cassette. The amplification product from the $1^{st}$ PCR gives the 5' fragment of 606 bp and was digested with NotI and BamHI to give a 588 bp 5' fragment.

The $2^{nd}$ PCR took place with the following oligonucleotide primers, which were derived from the sequence hTR (FIG. 1):

```
5' CGCGGATCCG ACTTGGTACC ATGAATGGGC AGTGAGCCGG 3' (TMK4)    (SEQ ID NO:12)

5' CCCAAGCTTG TGGGGGTTAT ATCCTA 3' (TMK2)                   (SEQ ID NO:10).
```

The oligonucleotide primer TMK4 (position 599–618, FIG. 6) contains an additional 5' extension of 20 bp with a BamHI and KpnI cleavage site and encodes 17 bp of the ClaI-BamHI-KpnI cassette. The amplification product from the $2^{nd}$ PCR gives the 3' fragment of 387 bp and was hydrolyzed with BamHI and HindIII to give a 375 bp 3' fragment. T4 ligase was used to connect the BamHI cleavage sites of the 5' and 3' fragments together to give the 963 bp NotI-HindIII fragment, which was cloned into the corresponding cleavage sites (position 12 and 38) of pGEM-13Zf(+) to create the 4118 bp construct pGEM-hTR(Ka) (FIG. 6). pGEM-hTR(Kb) and pGEM-hTR(Kc) were constructed by replacing a 29 bp sequence in the construct pGEM-hTR(Ka) (position 587–615) by a randomized sequence of 29 bp. A selective restriction digestion with ClaI and KpnI on the construct pGEM-hTR(Ka) and the following oligonucleotides Kb and Kc

```
           ClaI                 KpnI        (SEQ ID NO:13)

5' CCATCGATTC CCGTCGCCAA ATCGAGCGGG TACCCC 3' Kb

3' GGTAGCTAAG GGCAGCGGTT TAGCTCGCCC ATGGGG 5'

ClaI                 KpnI        (SEQ ID NO:14)

5' CCATCGATCG TCCAATCGCT ATACTCTCGG TACCCC 3' Kc

3' GGTAGCTAGC AGGTTAGCGA TATGAGAGCC ATGGGG 5'
``` was followed by cloning, in two separate T4 ligase reactions, the ClaI-KpnI fragment of the oligonucleotides Kb and Kc into the corresponding cleavage sites of pGEM-hTR(Ka) to create the 4118 bp constructs pGEM-hTR(Kb) and pGEM-hTR(Kc).

RNA was produced in vitro in a length of 975 bp from pGEM-hTR(Ka) (hTRKa, FIG. 7), pGEM-hTR(Kb) (hTRKb, FIG. 8) and pGEM-hTR(Kc) (hTRKc, FIG. 9) with Sp6 RNA polymerase. The further processing of the RNA, such as DNase digestion, purification and calibration, took place by standard methods.

5. Results

Figure 2:
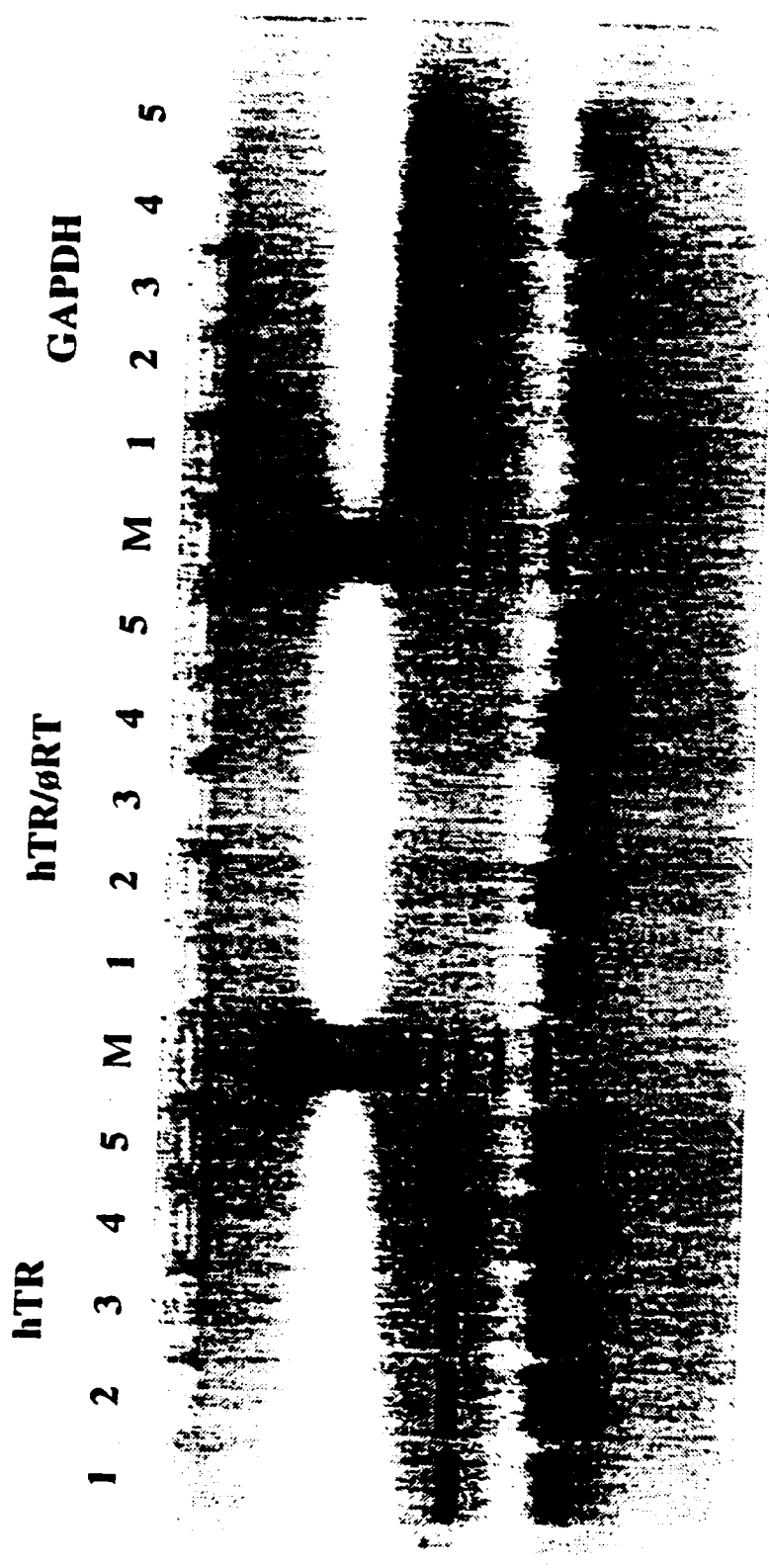
FIG. 2 shows a PCR amplification on the cDNA of tumor cell lines.

The investigations on tumor cell lines revealed that the RNA component of human telomerase was detectable in different amounts in all the tumor cell lines with the same amount amplified in the GAPDH control reaction (FIG. 2). It was possible to rule out contamination with genomic DNA in each case by a control reaction without addition of reverse transcriptase.

The comparative investigations on tumor tissue and healthy tissue revealed that the RNA component of human telomerase could be detected unambiguously in tumor tissues but not in healthy reference tissues (FIG. 3). The variation in intensity of the amplification products can be explained by the individual quality of the RNA obtained from the tumor tissues.

The investigations with venous blood revealed that different levels of telomerase activities were detectable in blood from healthy subjects and from leukemia patients, with distinctly lower telomerase activities being found in the control subjects by comparison with the cancer patients (FIG. 4).

The in vitro transcription using Sp6 RNA polymerase on the constructs pGEM-hTR(Ka), pGEM-hTR(Kb) and pGEM-hTR(Kc) revealed in each case the required RNA transcript hTRKa, hTRKb and hTRKc with a length of 975 bases.

What is claimed is:

1. A method for the detection of metastatic tumor cells in a blood sample, comprising:
   (a) removing the non tumor cells from the sample;
   (b) specifically amplifying the RNA component of telomerase in the sample; and
   (c) determining quantitatively the amount of amplified nucleic acid to thereby detect the presence of tumor cells in the blood sample, wherein the detection of tumor cells is indicative of metastasis.

2. The method of claim 1, wherein prior to the amplification of the RNA, the RNA contained in the sample is reverse transcribed into cDNA.

3. The method of claim 2, wherein prior to reverse transcription of the RNA, the sample is treated with DNase.

4. The method of claim 1, wherein prior to step (b), the RNA contained in the sample is purified.

5. The method of claim 4, wherein purification is effected by ion exchange chromatography.

6. The method of claim 4, wherein purification is effected on silica gel.

7. The method of claim 1, wherein, for quantitative determination of the amplified nucleic acid, at least one, optionally three, standard nucleic acids are coamplified and are added in different concentrations to the sample.

8. The method of claim 7, wherein the coamplifying standard nucleic acids(s) comprise one or more of the sequences of nucleotides set forth in any of FIGS. 7, 8 and 9.

9. The method of claim 7, wherein, quantification is effected by comparing the amount of coamplified nucleic acid or nucleic acids with the amount of the amplified nucleic acid.

10. The method of claim 1, wherein the amplified nucleic acids are quantified either directly or via a label.

11. The method of claim 10, wherein the label is selected from the group consisting of a radioactive label, a biotin label, a fluorescent label and an electrochemoluminescent label.

12. The method of claim 1, wherein the amplified nucleic acids are detected via a hybridization with a labeled oligonucleotide.

13. The method of claim 12, wherein the label is selected from the group consisting of a radioactive label, a biotin label, a fluorescent label and an electrochemoluminescent label.

14. The method of claim 1, wherein the sample is peripheral blood, and wherein a nucleic acid, different from the amplified nucleic acid and known to be present in peripheral blood, is specifically coamplified with the RNA component and detected as a positive control for the amplification of the RNA component.

15. The method of claim 14, wherein the nucleic acid that is amplified as a positive control is selected from mRNA coding for β-globin and glyceraldehyde-phosphate dehydrogenase.

16. The method of claim 1, wherein, as a negative control, no reverse transcription reaction is carried out before the amplification reaction with the sample and/or water is employed in place of the blood.

17. The method of claim 1, wherein the following oligonucleotide primers are used for the amplification:

```
5' GACTCGGCTC ACACATGCAG TTCGC 3'    (TM1) and/   (SEQ ID NO. 1)
                                              or
5' CTGGTCGAGA TCTACCTTGG GAGAAGC 3'   (TM2)        (SEQ ID NO. 2)
```

18. The method of claim 17, wherein TM1 and/or TM2 comprises an RNA polymerase promoter.

19. The method of claim 1, wherein a DNA polymerase or an RNA polymerase is used for the amplification.

20. The method of claim 19, wherein, amplification with DNA polymerase is effected by the polymerase chain reaction (PCR) and, amplification with RNA polymerase is effected by isothermal nucleic acid sequence-based amplification (NASBA).

21. The method of claim 1, wherein any tumor cells in the blood sample are concentrated.

22. The method of claim 21, wherein concentration is effected by immunoabsorption.

23. The method of claim 1, wherein the amount of amplified nucleic acid is determined in a venous blood sample and in an arterial blood sample, and the results are compared with one another.

24. The method of claim 1, wherein:
the amount of amplified nucleic acid is determined in a blood sample from a finger pad, and in a venous or arterial blood sample, and the results are compared with one another.

25. The method of claim 1, wherein the tumor cells are metastases of malignant tumors.

26. The method of claim 25, wherein the tumor cells are micrometastases.

27. The method of claim 1, wherein the tumor cells are from metastasizing tumors and/or neoplasms, from a T-cell lymphoblastoma, T-cell leukemia cells, chronic myeloid leukemia cells, acute lymphatic leukemia cells, chronic lymphatic leukemia cells, tetratocarcinoma, melanoma, carcinoma of the lung, large intestine cancer, breast cancer, hepatocellular carcinoma, kidney tumor, adrenal tumor, prostate carcinoma, neuroblastoma, brain tumor, rhabdomyosarcoma, leilomyasarcoma and lymphoma.

28. The method of claim 1, wherein removal of non tumor cells is effected by immunoabsorption.

29. The method of claim 1, further comprising quantification of any tumor cells in the sample.

30. The method of claim 1, wherein the detection of tumor cells is indicative of incipient metastasis.

31. The method of claim 1, wherein the detection of tumor cells is effected before organ metastases become manifest.

32. The method of claim 1, wherein the detection of tumor cells is indicative of the efficacy of cancer therapy.

33. The method of claim 1, wherein the non tumor cells are stem cells and/or activated immune cells.

* * * * *

UNITED STATES PATENT AND TRADEMARK OFFICE
CERTIFICATE OF CORRECTION

PATENT NO. : 6,582,904 B2
DATED : June 24, 2003
INVENTOR(S) : Michael Dahm

It is certified that error appears in the above-identified patent and that said Letters Patent is hereby corrected as shown below:

Title page,
Item [56], References Cited, OTHER PUBLICATIONS, please insert:
-- Zhong *et al.*, Sensitivity and Specificity of Immunocytochemistry for the Detection of Tumour Cells in the Bone Marrow of Patients with Breast Cancer, *Tumordiagn. u. Ther.* 20:39-44 (1999). --
Please replace "Iliyama" with -- Hiyama -- in "Iliyama et al., "Alternations in telomeric repeat length in lung cancer are associated with loss of heterozygosity in p53 and Rb" *Oncogene* 10:937-944 (1995)."
Please replace "Iliguchi R." with -- Higuchi R. -- in "Iliguchi R., Recombinant PCR, PCR Protocols: A Guide to Methods and Applications Academic Press, Inc., pp. 177-183 (1990)."

Column 36,
Lines 1-10, please replace Claim 26 and 27 with the following:
  26. The method of claim 25, wherein the metastases are micrometastases.
  27. The method of claim 1, wherein the tumor cells are from metastasizing tumors and/or neoplasms, selected from a T-cell lymphoblastoma, T-cell leukemia cells, chronic myeloid leukemia cells, acute lymphatic leukemia cells, chronic lymphatic leukemia cells, teratocarcinoma, melanoma, carcinoma of the lung, large intestine cancer, breast cancer, hepatocellular carcinoma, kidney tumor, adrenal tumor, prostate carcinoma, neuroblastoma, brain tumor, rhabdomyosarcoma, leilomyasarcoma and lymphoma.

Signed and Sealed this

Twenty-seventh Day of January, 2004

JON W. DUDAS
*Acting Director of the United States Patent and Trademark Office*

```
                         SEQUENCE LISTING (1) GENERAL INFORMATION:

(iii) NUMBER OF SEQUENCES: 21

(2) INFORMATION FOR SEQ ID NO:  1:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:   1:

GACTCGGCTC ACACATGCAG TTCGC                                              25

(2) INFORMATION FOR SEQ ID NO:  2:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:   2:

CTGGTCGAGA TCTACCTTGG GAGAAGC                                            27

(2) INFORMATION FOR SEQ ID NO:  3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:   3:

CGACTTTGGA GGTGCCTTCA                                                    20

(2) INFORMATION FOR SEQ ID NO:  4:

(i) SEQUENCE CHARACTERISTICS:
          (A) LENGTH: 20 base pairs
          (B) TYPE: nucleic acid
          (C) STRANDEDNESS: single
          (D) TOPOLOGY: linear
```

(ii) MOLECULE TYPE: Genomic DNA (xi) SEQUENCE DESCRIPTION: SEQ ID NO: 4:

AAGTCGGATC CACTTAGGTC                                                    20

(2) INFORMATION FOR SEQ ID NO: 5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 5:

CGCTCGATTT GGCGACGGGA                                                    20

(2) INFORMATION FOR SEQ ID NO: 6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 6:

GAGAGTATAG CGATTGGACG                                                    20

(2) INFORMATION FOR SEQ ID NO: 7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 7:

ACCCAGAGGT TCTTTGAGTC                                                    20

(2) INFORMATION FOR SEQ ID NO: 8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 8:

TCTGATAGGC AGCCTGCACT                                                    20

(2) INFORMATION FOR SEQ ID NO: 9:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: Genomic DNA (xi) SEQUENCE DESCRIPTION: SEQ ID NO: 9:

ATAAGAATGC GGCCGCGGGT TGCGGAGGGT GGGCCTGGGA GGG                43

(2) INFORMATION FOR SEQ ID NO: 10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 10:

CCCAAGCTTG TGGGGGTTAT ATCCTA                                  26

(2) INFORMATION FOR SEQ ID NO: 11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 11:

CGCGGATCCA CTTAGGTCAT CGATCTGCCA ATTTGCAGCA CACT              44

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 12:

CGCGGATCCG ACTTGGTACC ATGAATGGGC AGTGAGCCGG                   40

(2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO: 13:

CCATCGATTC CCGTCGCCAA ATCGAGCGGG TACCCC                       36

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO: 14:

CCATCGATCG TCCAATCGCT ATACTCTCGG TACCCC                       36

(2) INFORMATION FOR SEQ ID NO: 15:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO: 15:

```
ATCGATGACC TAAGTGGATC CGACTTGGTA CC                                       32
```

(2) INFORMATION FOR SEQ ID NO: 16:

(i) SEQUENCE CHARACTERISTICS:
        (A) LENGTH: 962 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 16:

```
GGGTTGCGGA GGGTGGGCCT GGGAGGGGTG GTGGCCATTT TTTGTCTAAC CCTAACTGAG         60
AAGGGCGTAG CGCCGTGCT TTTGCTCCCC GCGCGCTGTT TTTCTCGCTG ACTTTCAGCG         120
GGCGGAAAAG CCTCGGCCTG CCGCCTTCCA CCGTTCATTC TAGAGCAAAC AAAAAATGTC        180
AGCTGCTGGC CCGTTCGCCT CCCGGGGACC TGCGGCGGGT CGCCTGCCCA GCCCCCGAAC        240
CCCGCCTGGA GCCGCGGTCG GCCCGGGGCT TCTCCGGAGG CACCCACTGC CACCGCGAAG        300
AGTTGGGCTC TGTCAGCCGC GGGTCTCTCG GGGGCGAGGG CGAGGTTCAC CGTTTCAGGC        360
CGCAGGAAGA GGAACGGAGC GAGTCCCGCC GCGGCGCGAT TCCCTGAGCT GTGGGACGTG        420
CACCCAGGAC TCGGCTCACA CATGCAGTTC GCTTTCCTGT TGGTGGGGGG AACGCCGATC        480
GTGCGCATCC GTCACCCCTC GCCGGCAGTG GGGGCTTGTG AACCCCCAAA CCTGACTGAC        540
TGGGCCAGTG TGCTGCAAAT TGGCAGGAGA CGTGAAGGCA CCTCCAAAGT CGGCCAAAAT        600
GAATGGGCAG TGAGCCGGGG TTGCCTGGAG CCGTTCCTGC GTGGGTTCTC CCGTCTTCCG        660
CTTTTTGTTG CCTTTTATGG TTGTATTACA ACTTAGTTCC TGCTCTGCAG ATTTTGTTGA        720
GGTTTTTGCT TCTCCCAAGG TAGATCTCGA CCAGTCCCTC AACGGGGTGT GGGGAGAACA        780
GTCATTTTTT TTTGAGAGAT CATTTAACAT TTAATGAATA TTTAATTAGA AGATCTAAAT       840
GAACATTGGA AATTGTGTTC CTTTAATGGT CATCGGTTTA TGCCAGAGGT TAGAAGTTTC        900
TTTTTTGAAA AATTAGACCT TGGCGATGAC CTTGAGCAGT AGGATATAAC CCCCACAAGC        960
TT                                                                     962
```

(2) INFORMATION FOR SEQ ID NO: 17:

(i) SEQUENCE CHARACTERISTICS:
        (A) LENGTH: 4118 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 17:

```
GGGCGAATTG GCGGCCGCGG GTTGCGGAGG GTGGGCCTGG GAGGGGTGGT GGCCATTTTT         60
TGTCTAACCC TAACTGAGAA GGGCGTAGGC GCCGTGCTTT TGCTCCCCGC GCGCTGTTTT        120
TCTCGCTGAC TTTCAGCGGG CGGAAAAGCC TCGGCCTGCC GCCTTCCACC GTTCATTCTA        180
```

-continued

```
GAGCAAACAA AAAATGTCAG CTGCTGGCCC GTTCGCCTCC CGGGGACCTG CGGCGGGTCG    240
CCTGCCCAGC CCCCGAACCC CGCCTGGAGC CGCGGTCGGC CCGGGGCTTC TCCGGAGGCA    300
CCCACTGCCA CCGCGAAGAG TTGGGCTCTG TCAGCCGCGG GTCTCTCGGG GGCGAGGGCG    360
AGGTTCACCG TTTCAGGCCG CAGGAAGAGG AACGGAGCGA GTCCCGCCGC GGCGCGATTC    420
CCTGAGCTGT GGGACGTGCA CCCAGGACTC GGCTCACACA TGCAGTTCGC TTTCCTGTTG    480
GTGGGGGGAA CGCCGATCGT GCGCATCCGT CACCCCTCGC CGGCAGTGGG GGCTTGTGAA    540
CCCCCAAACC TGACTGACTG GGCCAGTGTG CTGCAAATTG CAGGAGACG TGAAGGCACC     600
TCCAAAGTCG GCCAAAATGA ATGGGCAGTG AGCCGGGGTT GCCTGGAGCC GTTCCTGCGT    660
GGGTTCTCCC GTCTTCCGCT TTTTGTTGCC TTTTATGGTT GTATTACAAC TTAGTTCCTG    720
CTCTGCAGAT TTTGTTGAGG TTTTTGCTTC TCCCAAGGTA GATCTCGACC AGTCCCTCAA    780
CGGGGTGTGG GAGAACAGT CATTTTTTTT TGAGAGATCA TTTAACATTT AATGAATATT     840
TAATTAGAAG ATCTAAATGA ACATTGGAAA TTGTGTTCCT TTAATGGTCA TCGGTTTATG    900
CCAGAGGTTA GAAGTTTCTT TTTTGAAAAA TTAGACCTTG GCGATGACCT TGAGCAGTAG    960
GATATAACCC CCACAAGCTT GAGTATTCTA TAGTGTCACC TAAATAGCTT GGCGTAATCA   1020
TGGTCATAGC TGTTTCCTGT GTGAAATTGT TATCCGCTCA CAATTCCACA ACATACGA     1080
GCCGGAAGCA TAAAGTGTAA AGCCTGGGGT GCCTAATGAG TGAGCTAACT CACATTAATT   1140
GCGTTGCGCT CACTGCCCGC TTTCCAGTCG GGAAACCTGT CGTGCCAGCT GCATTAATGA   1200
ATCGGCCAAC GCGCGGGGAG AGGCGGTTTG CGTATTGGGC GCTCTTCCGC TTCCTCGCTC   1260
ACTGACTCGC TGCGCTCGGT CGTTCGGCTG CGGCGAGCGG TATCAGCTCA CTCAAAGGCG   1320
GTAATACGGT TATCCACAGA ATCAGGGGAT AACGCAGGAA AGAACATGTG AGCAAAAGGC   1380
CAGCAAAAGG CCAGGAACCG TAAAAAGGCC GCGTTGCTGG CGTTTTTCCA TAGGCTCCGC   1440
CCCCCTGACG AGCATCACAA AAATCGACGC TCAAGTCAGA GGTGGCGAAA CCCGACAGGA   1500
CTATAAAGAT ACCAGGCGTT TCCCCCTGGA AGCTCCCTCG TGCGCTCTCC TGTTCCGACC   1560
CTGCCGCTTA CCGGATACCT GTCCGCCTTT CTCCCTTCGG GAAGCGTGGC GCTTTCTCAT   1620
AGCTCACGCT GTAGGTATCT CAGTTCGGTG TAGGTCGTTC GCTCCAAGCT GGGCTGTGTG   1680
CACGAACCCC CCGTTCAGCC CGACCGCTGC GCCTTATCCG GTAACTATCG TCTTGAGTCC   1740
AACCCGGTAA GACACGACTT ATCGCCACTG GCAGCAGCCA CTGGTAACAG GATTAGCAGA   1800
GCGAGGTATG TAGGCGGTGC TACAGAGTTC TTGAAGTGGT GGCCTAACTA CGGCTACACT   1860
AGAAGGACAG TATTTGGTAT CTGCGCTCTG CTGAAGCCAG TTACCTTCGG AAAAAGAGTT   1920
GGTAGCTCTT GATCCGGCAA ACAAACCACC GCTGGTAGCG GTGGTTTTTT TGTTTGCAAG   1980
CAGCAGATTA CGCGCAGAAA AAAAGGATCT CAAGAAGATC CTTTGATCTT TTCTACGGGG   2040
TCTGACGCTC AGTGGAACGA AAACTCACGT TAAGGGATTT TGGTCATGAG ATTATCAAAA   2100
AGGATCTTCA CCTAGATCCT TTTAAATTAA AAATGAAGTT TTAAATCAAT CTAAAGTATA   2160
TATGAGTAAA CTTGGTCTGA CAGTTACCAA TGCTTAATCA GTGAGGCACC TATCTCAGCG   2220
ATCTGTCTAT TTCGTTCATC CATAGTTGCC TGACTCCCCG TCGTGTAGAT AACTACGATA   2280
CGGGAGGGCT TACCATCTGG CCCCAGTGCT GCAATGATAC CGCGAGACCC ACGCTCACCG   2340
GCTCCAGATT TATCAGCAAT AAACCAGCCA GCCGGAAGGG CCGAGCGCAG AAGTGGTCCT   2400
GCAACTTTAT CCGCCTCCAT CCAGTCTATT AATTGTTGCC GGGAAGCTAG AGTAAGTAGT   2460
TCGCCAGTTA ATAGTTTGCG CAACGTTGTT GCCATTGCTA CAGGCATCGT GGTGTCACGC   2520
```

-continued

```
TCGTCGTTTG GTATGGCTTC ATTCAGCTCC GGTTCCCAAC GATCAAGGCG AGTTACATGA    2580

TCCCCCATGT TGTGCAAAAA AGCGGTTAGC TCCTTCGGTC CTCCGATCGT TGTCAGAAGT    2640

AAGTTGGCCG CAGTGTTATC ACTCATGGTT ATGGCAGCAC TGCATAATTC TCTTACTGTC    2700

ATGCCATCCG TAAGATGCTT TTCTGTGACT GGTGAGTACT CAACCAAGTC ATTCTGAGAA    2760

TAGTGTATGC GGCGACCGAG TTGCTCTTGC CCGGCGTCAA TACGGGATAA TACCGCGCCA    2820

CATAGCAGAA CTTTAAAAGT GCTCATCATT GGAAAACGTT CTTCGGGGCG AAAACTCTCA    2880

AGGATCTTAC CGCTGTTGAG ATCCAGTTCG ATGTAACCCA CTCGTGCACC CAACTGATCT    2940

TCAGCATCTT TTACTTTCAC CAGCGTTTCT GGGTGAGCAA AAACAGGAAG GCAAAATGCC    3000

GCAAAAAAGG GAATAAGGGC GACACGGAAA TGTTGAATAC TCATACTCTT CCTTTTTCAA    3060

TATTATTGAA GCATTTATCA GGGTTATTGT CTCATGAGCG GATACATATT TGAATGTATT    3120

TAGAAAAATA AACAAATAGG GGTTCCGCGC ACATTTCCCC GAAAAGTGCC ACCTGACGTC    3180

TAAGAAACCA TTATTATCAT GACATTAACC TATAAAAATA GGCGTATCAC GAGGCCCTTT    3240

CGTCTCGCGC GTTTCGGTGA TGACGGTGAA AACCTCTGAC ACATGCAGCT CCCGGAGACG    3300

GTCACAGCTT GTCTGTAAGC GGATGCCGGG AGCAGACAAG CCCGTCAGGG CGCGTCAGCG    3360

GGTGTTGGCG GGTGTCGGGG CTGGCTTAAC TATGCGGCAT CAGAGCAGAT TGTACTGAGA    3420

GTGCACCATA TGCGGTGTGA AATACCGCAC AGATGCGTAA GGAGAAAATA CCGCATCAGG    3480

CGAAATTGTA AACGTTAATA TTTTGTTAAA ATTCGCGTTA AATATTTGTT AAATCAGCTC    3540

ATTTTTTAAC CAATAGGCCG AAATCGGCAA AATCCCTTAT AAATCAAAAG AATAGACCGA    3600

GATAGGGTTG AGTGTTGTTC CAGTTTGGAA CAAGAGTCCA CTATTAAAGA ACGTGGACTC    3660

CAACGTCAAA GGGCGAAAAA CCGTCTATCA GGGCGATGGC CCACTACGTG AACCATCACC    3720

CAAATCAAGT TTTTTGCGGT CGAGGTGCCG TAAAGCTCTA AATCGGAACC CTAAAGGGAG    3780

CCCCCGATTT AGAGCTTGAC GGGGAAAGCC GGCGAACGTG GCGAGAAAGG AAGGGAAGAA    3840

AGCGAAAGGA GCGGGCGCTA GGGCGCTGGC AAGTGTAGCG GTCACGCTGC GCGTAACCAC    3900

CACACCCGCC GCGCTTAATG CGCCGCTACA GGGCGCGTCC ATTCGCCATT CAGGCTGCGC    3960

AACTGTTGGG AAGGGCGATC GGTGCGGGCC TCTTCGCTAT TACGCCAGCT GGCGAAAGGG    4020

GGATGTGCTG CAAGGCGATT AAGTTGGGTA ACGCCAGGGT TTTCCCAGTC ACGACGTTGT    4080

AAAACGACGG CCAGTGAATT GTAATACGAC TCACTATA                           4118
```

(2) INFORMATION FOR SEQ ID NO: 18:

(i) SEQUENCE CHARACTERISTICS:
        (A) LENGTH: 4118 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 18:

```
GGGCGAATTG GCGGCCGCGG GTTGCGGAGG GTGGGCCTGG GAGGGGTGGT GGCCATTTTT      60

TGTCTAACCC TAACTGAGAA GGGCGTAGGC GCCGTGCTTT TGCTCCCCGC GCGCTGTTTT     120

TCTCGCTGAC TTTCAGCGGG CGGAAAAGCC TCGGCCTGCC GCCTTCCACC GTTCATTCTA     180

GAGCAAACAA AAAATGTCAG CTGCTGGCCC GTTCGCCTCC CGGGGACCTG CGGCGGGTCG     240

CCTGCCCAGC CCCCGAACCC CGCCTGGAGC CGCGGTCGGC CCGGGGCTTC TCCGGAGGCA     300

CCCACTGCCA CCGCGAAGAG TTGGGCTCTG TCAGCCGCGG GTCTCTCGGG GGCGAGGGCG     360
```

```
AGGTTCACCG TTTCAGGCCG CAGGAAGAGG AACGGAGCGA GTCCCGCCGC GGCGCGATTC    420

CCTGAGCTGT GGGACGTGCA CCCAGGACTC GGCTCACACA TGCAGTTCGC TTTCCTGTTG    480

GTGGGGGAA CGCCGATCGT GCGCATCCGT CACCCCTCGC CGGCAGTGGG GGCTTGTGAA     540

CCCCCAAACC TGACTGACTG GGCCAGTGTG CTGCAAATTG GCAGATCGAT GACCTAAGTG    600

GATCCGACTT GGTACCATGA ATGGGCAGTG AGCCGGGGTT GCCTGGAGCC GTTCCTGCGT    660

GGGTTCTCCC GTCTTCCGCT TTTTGTTGCC TTTTATGGTT GTATTACAAC TTAGTTCCTG    720

CTCTGCAGAT TTTGTTGAGG TTTTTGCTTC TCCCAAGGTA GATCTCGACC AGTCCCTCAA    780

CGGGGTGTGG GGAGAACAGT CATTTTTTTT TGAGAGATCA TTTAACATTT AATGAATATT    840

TAATTAGAAG ATCTAAATGA ACATTGGAAA TTGTGTTCCT TTAATGGTCA TCGGTTTATG    900

CCAGAGGTTA GAAGTTTCTT TTTTGAAAAA TTAGACCTTG GCGATGACCT TGAGCAGTAG    960

GATATAACCC CCACAAGCTT GAGTATTCTA TAGTGTCACC TAAATAGCTT GGCGTAATCA   1020

TGGTCATAGC TGTTTCCTGT GTGAAATTGT TATCCGCTCA CAATTCCACA CAACATACGA   1080

GCCGAAGCA TAAAGTGTAA AGCCTGGGGT GCCTAATGAG TGAGCTAACT CACATTAATT    1140

GCGTTGCGCT CACTGCCCGC TTTCCAGTCG GGAAACCTGT CGTGCCAGCT GCATTAATGA   1200

ATCGGCCAAC GCGCGGGGAG AGGCGGTTTG CGTATTGGGC GCTCTTCCGC TTCCTCGCTC   1260

ACTGACTCGC TGCGCTCGGT CGTTCGGCTG CGGCGAGCGG TATCAGCTCA CTCAAAGGCG   1320

GTAATACGGT TATCCACAGA ATCAGGGGAT AACGCAGGAA AGAACATGTG AGCAAAAGGC   1380

CAGCAAAAGG CCAGGAACCG TAAAAAGGCC GCGTTGCTGG CGTTTTTCCA TAGGCTCCGC   1440

CCCCCTGACG AGCATCACAA AAATCGACGC TCAAGTCAGA GGTGGCGAAA CCCGACAGGA   1500

CTATAAAGAT ACCAGGCGTT TCCCCCTGGA AGCTCCCTCG TGCGCTCTCC TGTTCCGACC   1560

CTGCCGCTTA CCGGATACCT GTCCGCCTTT CTCCCTTCGG GAAGCGTGGC GCTTTCTCAT   1620

AGCTCACGCT GTAGGTATCT CAGTTCGGTG TAGGTCGTTC GCTCCAAGCT GGGCTGTGTG   1680

CACGAACCCC CCGTTCAGCC CGACCGCTGC GCCTTATCCG GTAACTATCG TCTTGAGTCC   1740

AACCCGGTAA GACACGACTT ATCGCCACTG GCAGCAGCCA CTGGTAACAG GATTAGCAGA   1800

GCGAGGTATG TAGGCGGTGC TACAGAGTTC TTGAAGTGGT GGCCTAACTA CGGCTACACT   1860

AGAAGGACAG TATTTGGTAT CTGCGCTCTG CTGAAGCCAG TTACCTTCGG AAAAAGAGTT   1920

GGTAGCTCTT GATCCGGCAA ACAAACCACC GCTGGTAGCG GTGGTTTTTT TGTTTGCAAG   1980

CAGCAGATTA CGCGCAGAAA AAAAGGATCT CAAGAAGATC CTTTGATCTT TTCTACGGGG   2040

TCTGACGCTC AGTGGAACGA AAACTCACGT TAAGGGATTT TGGTCATGAG ATTATCAAAA   2100

AGGATCTTCA CCTAGATCCT TTTAAATTAA AAATGAAGTT TTAAATCAAT CTAAAGTATA   2160

TATGAGTAAA CTTGGTCTGA CAGTTACCAA TGCTTAATCA GTGAGGCACC TATCTCAGCG   2220

ATCTGTCTAT TTCGTTCATC CATAGTTGCC TGACTCCCCG TCGTGTAGAT AACTACGATA   2280

CGGGAGGGCT TACCATCTGG CCCCAGTGCT GCAATGATAC CGCGAGACCC ACGCTCACCG   2340

GCTCCAGATT TATCAGCAAT AAACCAGCCA GCCGGAAGGG CCGAGCGCAG AAGTGGTCCT   2400

GCAACTTTAT CCGCCTCCAT CCAGTCTATT AATTGTTGCC GGGAAGCTAG AGTAAGTAGT   2460

TCGCCAGTTA ATAGTTTGCG CAACGTTGTT GCCATTGCTA CAGGCATCGT GGTGTCACGC   2520

TCGTCGTTTG GTATGGCTTC ATTCAGCTCC GGTTCCCAAC GATCAAGGCG AGTTACATGA   2580

TCCCCCATGT TGTGCAAAAA AGCGGTTAGC TCCTTCGGTC CTCCGATCGT TGTCAGAAGT   2640

AAGTTGGCCG CAGTGTTATC ACTCATGGTT ATGGCAGCAC TGCATAATTC TCTTACTGTC   2700

ATGCCATCCG TAAGATGCTT TTCTGTGACT GGTGAGTACT CAACCAAGTC ATTCTGAGAA   2760
```

```
TAGTGTATGC GGCGACCGAG TTGCTCTTGC CCGGCGTCAA TACGGGATAA TACCGCGCCA    2820

CATAGCAGAA CTTTAAAAGT GCTCATCATT GGAAAACGTT CTTCGGGCG AAAACTCTCA     2880

AGGATCTTAC CGCTGTTGAG ATCCAGTTCG ATGTAACCCA CTCGTGCACC CAACTGATCT    2940

TCAGCATCTT TTACTTTCAC CAGCGTTTCT GGGTGAGCAA AAACAGGAAG GCAAAATGCC    3000

GCAAAAAAGG GAATAAGGGC GACACGGAAA TGTTGAATAC TCATACTCTT CCTTTTTCAA    3060

TATTATTGAA GCATTTATCA GGGTTATTGT CTCATGAGCG GATACATATT TGAATGTATT    3120

TAGAAAAATA AACAAATAGG GGTTCCGCGC ACATTTCCCC GAAAAGTGCC ACCTGACGTC    3180

TAAGAAACCA TTATTATCAT GACATTAACC TATAAAAATA GGCGTATCAC GAGGCCCTTT    3240

CGTCTCGCGC GTTTCGGTGA TGACGGTGAA AACCTCTGAC ACATGCAGCT CCCGGAGACG    3300

GTCACAGCTT GTCTGTAAGC GGATGCCGGG AGCAGACAAG CCCGTCAGGG CGCGTCAGCG    3360

GGTGTTGGCG GGTGTCGGGG CTGGCTTAAC TATGCGGCAT CAGAGCAGAT TGTACTGAGA    3420

GTGCACCATA TGCGGTGTGA AATACCGCAC AGATGCGTAA GGAGAAAATA CCGCATCAGG    3480

CGAAATTGTA AACGTTAATA TTTTGTTAAA ATTCGCGTTA AATATTTGTT AAATCAGCTC    3540

ATTTTTTAAC CAATAGGCCG AAATCGGCAA AATCCCTTAT AAATCAAAAG AATAGACCGA    3600

GATAGGGTTG AGTGTTGTTC CAGTTTGGAA CAAGAGTCCA CTATTAAAGA ACGTGGACTC    3660

CAACGTCAAA GGGCGAAAAA CCGTCTATCA GGGCGATGGC CCACTACGTG AACCATCACC    3720

CAAATCAAGT TTTTTGCGGT CGAGGTGCCG TAAAGCTCTA AATCGGAACC CTAAAGGGAG    3780

CCCCCGATTT AGAGCTTGAC GGGGAAAGCC GGCGAACGTG GCGAGAAAGG AAGGGAAGAA    3840

AGCGAAAGGA GCGGGCGCTA GGGCGCTGGC AAGTGTAGCG GTCACGCTGC GCGTAACCAC    3900

CACACCCGCC GCGCTTAATG CGCCGCTACA GGGCGCGTCC ATTCGCCATT CAGGCTGCGC    3960

AACTGTTGGG AAGGGCGATC GGTGCGGGCC TCTTCGCTAT TACGCCAGCT GGCGAAAGGG    4020

GGATGTGCTG CAAGGCGATT AAGTTGGGTA ACGCCAGGGT TTTCCCAGTC ACGACGTTGT    4080

AAAACGACGG CCAGTGAATT GTAATACGAC TCACTATA                           4118

(2) INFORMATION FOR SEQ ID NO: 19:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: Genomic RNA (xi) SEQUENCE DESCRIPTION: SEQ ID NO: 19:

GGGCGAAUUG GCGGCCGCGG GUUGCGGAGG GUGGGCCUGG GAGGGGUGGU GGCCAUUUUU      60

UGUCUAACCC UAACUGAGAA GGGCGUAGGC GCCGUGCUUU UGCUCCCCGC GCGCUGUUUU     120

UCUCGCUGAC UUUCAGCGGG CGGAAAAGCC UCGGCCUGCC GCCUUCCACC GUUCAUUCUA     180

GAGCAAACAA AAAAUGUCAG CUGCUGGCCC GUUCGCCUCC CGGGGACCUG CGGCGGGUCG     240

CCUGCCCAGC CCCCGAACCC CGCCUGGAGC CGCGGUCGGC CCGGGGCUUC UCCGGAGGCA     300

CCCACUGCCA CCGCGAAGAG UUGGGCUCUG UCAGCCGCGG GUCUCUCGGG GGCGAGGGCG     360

AGGUUCACCG UUUCAGGCCG CAGGAAGAGG AACGGAGCGA GUCCCGCCGC GGCGCGAUUC     420

CCUGAGCUGU GGGACGUGCA CCCAGGACUC GGCUCACACA UGCAGUUCGC UUUCCUGUUG     480

GUGGGGGGAA CGCCGAUCGU GCGCAUCCGU CACCCCUCGC CGGCAGUGGG GGCUUGUGAA     540

CCCCCAAACC UGACUGACUG GGCCAGUGUG CUGCAAAUUG GCAGAUCGAU GACCUAAGUG     600
```

-continued

```
GAUCCGACUU GGUACCAUGA AUGGGCAGUG AGCCGGGGUU GCCUGGAGCC GUUCCUGCGU      660

GGGUUCUCCC GUCUUCCGCU UUUUGUUGCC UUUUAUGGUU GUAUUACAAC UUAGUUCCUG      720

CUCUGCAGAU UUUGUUGAGG UUUUUGCUUC UCCCAAGGUA GAUCUCGACC AGUCCCUCAA      780

CGGGGUGUGG GGAGAACAGU CAUUUUUUUU UGAGAGAUCA UUUAACAUUU AAUGAAUAUU      840

UAAUUAGAAG AUCUAAAUGA ACAUUGGAAA UUGUGUUCCU UUAAUGGUCA UCGGUUUAUG      900

CCAGAGGUUA GAAGUUUCUU UUUUGAAAAA UUAGACCUUG GCGAUGACCU UGAGCAGUAG      960

GAUAUAACCC CCACA                                                      975
```

(2) INFORMATION FOR SEQ ID NO: 20:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: Genomic RNA (xi) SEQUENCE DESCRIPTION: SEQ ID NO: 20:

```
GGGCGAAUUG GCGGCCGCGG GUUGCGGAGG GUGGGCCUGG GAGGGUGGU GGCCAUUUUU        60

UGUCUAACCC UAACUGAGAA GGGCGUAGGC GCCGUGCUUU UGCUCCCCGC GCGCUGUUUU      120

UCUCGCUGAC UUUCAGCGGG CGGAAAAGCC UCGGCCUGCC GCCUUCCACC GUUCAUUCUA      180

GAGCAAACAA AAAAUGUCAG CUGCUGGCCC GUUCGCCUCC CGGGGACCUG CGGCGGGUCG      240

CCUGCCCAGC CCCCGAACCC CGCCUGGAGC CGCGGUCGGC CCGGGGCUUC UCCGGAGGCA      300

CCCACUGCCA CCGCGAAGAG UUGGGCUCUG UCAGCCGCGG GUCUCUCGGG GGCGAGGGCG      360

AGGUUCACCG UUUCAGGCCG CAGGAAGAGG AACGGAGCGA GUCCGCCGC GGCGCGAUUC       420

CCUGAGCUGU GGGACGUGCA CCCAGGACUC GGCUCACACA UGCAGUUCGC UUUCCUGUUG      480

GUGGGGGGAA CGCCGAUCGU GCGCAUCCGU CACCCCUCGC CGGCAGUGGG GGCUUGUGAA      540

CCCCCAAACC UGACUGACUG GGCCAGUGUG CUGCAAAUUG GCAGAUCGAU UCCCGUCGCC      600

AAAUCGAGCG GGUACCAUGA AUGGGCAGUG AGCCGGGGUU GCCUGGAGCC GUUCCUGCGU      660

GGGUUCUCCC GUCUUCCGCU UUUUGUUGCC UUUUAUGGUU GUAUUACAAC UUAGUUCCUG      720

CUCUGCAGAU UUUGUUGAGG UUUUUGCUUC UCCCAAGGUA GAUCUCGACC AGUCCCUCAA      780

CGGGGUGUGG GGAGAACAGU CAUUUUUUUU UGAGAGAUCA UUUAACAUUU AAUGAAUAUU      840

UAAUUAGAAG AUCUAAAUGA ACAUUGGAAA UUGUGUUCCU UUAAUGGUCA UCGGUUUAUG      900

CCAGAGGUUA GAAGUUUCUU UUUUGAAAAA UUAGACCUUG GCGAUGACCU UGAGCAGUAG      960

GAUAUAACCC CCACA                                                      975
```

(2) INFORMATION FOR SEQ ID NO: 21:

(i) SEQUENCE CHARACTERISTICS:
        (A) LENGTH: 975 base pairs
        (B) TYPE: nucleic acid
        (C) STRANDEDNESS: single
        (D) TOPOLOGY: linear (ii) MOLECULE TYPE: Genomic RNA (xi) SEQUENCE DESCRIPTION: SEQ ID NO: 21:

```
GGGCGAAUUG GCGGCCGCGG GUUGCGGAGG GUGGGCCUGG GAGGGUGGU GGCCAUUUUU        60

UGUCUAACCC UAACUGAGAA GGGCGUAGGC GCCGUGCUUU UGCUCCCCGC GCGCUGUUUU      120
```

-continued

| | | | | | |
|---|---|---|---|---|---|
| UCUCGCUGAC | UUUCAGCGGG | CGGAAAAGCC | UCGGCCUGCC | GCCUUCCACC | GUUCAUUCUA | 180
| GAGCAAACAA | AAAAUGUCAG | CUGCUGGCCC | GUUCGCCUCC | CGGGGACCUG | CGGCGGGUCG | 240
| CCUGCCCAGC | CCCCGAACCC | CGCCUGGAGC | CGCGGUCGGC | CCGGGGCUUC | UCCGGAGGCA | 300
| CCCACUGCCA | CCGCGAAGAG | UUGGGCUCUG | UCAGCCGCGG | GUCUCUCGGG | GGCGAGGGCG | 360
| AGGUUCACCG | UUUCAGGCCG | CAGGAAGAGG | AACGGAGCGA | GUCCCGCCGC | GGCGCGAUUC | 420
| CCUGAGCUGU | GGGACGUGCA | CCCAGGACUC | GGCUCACACA | UGCAGUUCGC | UUUCCUGUUG | 480
| GUGGGGGAA | CGCCGAUCGU | GCGCAUCCGU | CACCCCUCGC | CGGCAGUGGG | GGCUUGUGAA | 540
| CCCCCAAACC | UGACUGACUG | GGCCAGUGUG | CUGCAAAUUG | GCAGAUCGAU | CGUCCAAUCG | 600
| CUAUACUCUC | GGUACCAUGA | AUGGGCAGUG | AGCCGGGGUU | GCCUGGAGCC | GUUCCUGCGU | 660
| GGGUUCUCCC | GUCUUCCGCU | UUUUGUUGCC | UUUUAUGGUU | GUAUUACAAC | UUAGUUCCUG | 720
| CUCUGCAGAU | UUUGUUGAGG | UUUUUGCUUC | UCCCAAGGUA | GAUCUCGACC | AGUCCCUCAA | 780
| CGGGGUGUGG | GGAGAACAGU | CAUUUUUUUU | UGAGAGAUCA | UUUAACAUUU | AAUGAAUAUU | 840
| UAAUUAGAAG | AUCUAAAUGA | ACAUUGGAAA | UUGUGUUCCU | UUAAUGGUCA | UCGGUUUAUG | 900
| CCAGAGGUUA | GAAGUUUCUU | UUUUGAAAAA | UUAGACCUUG | GCGAUGACCU | UGAGCAGUAG | 960
| GAUAUAACCC | CCACA | | | | | 975